(12) United States Patent
Lawton

(10) Patent No.: US 8,979,263 B2
(45) Date of Patent: Mar. 17, 2015

(54) DIAGNOSING AND REMEDIATING COGNITIVE DEFICITS INVOLVING ATTENTION, SEQUENTIAL PROCESSING, READING, SPEED OF PROCESSING, AND NAVIGATION

(76) Inventor: Teri A. Lawton, Del Mar, CA (US)

( * ) Notice: Subject to any disclaimer, the term of this patent is extended or adjusted under 35 U.S.C. 154(b) by 784 days.

(21) Appl. No.: 12/754,458

(22) Filed: Apr. 5, 2010

(65) Prior Publication Data

US 2010/0253905 A1   Oct. 7, 2010

Related U.S. Application Data

(60) Provisional application No. 61/166,997, filed on Apr. 6, 2009.

(51) Int. Cl.
```
A61B 3/00      (2006.01)
A61B 13/00     (2006.01)
A61B 3/032     (2006.01)
A61B 3/02      (2006.01)
G09B 19/00     (2006.01)
A61H 5/00      (2006.01)
```

(52) U.S. Cl.
CPC .................. *A61B 3/032* (2013.01); *A61B 3/022* (2013.01); *G09B 19/00* (2013.01); *A61H 5/00* (2013.01)
USPC ............................ 351/200; 351/203; 600/558

(58) Field of Classification Search
USPC ......... 351/200, 203–206, 210, 211, 222, 223, 351/224; 600/223, 558
See application file for complete search history.

(56) References Cited

U.S. PATENT DOCUMENTS

| | | | | |
|---|---|---|---|---|
| 5,109,425 | A | * | 4/1992 | Lawton .......................... 382/107 |
| 5,745,173 | A | * | 4/1998 | Edwards et al. ........... 348/208.4 |
| 6,045,515 | A | | 4/2000 | Lawton |
| 6,213,956 | B1 | * | 4/2001 | Lawton .......................... 600/558 |
| 7,773,097 | B2 | * | 8/2010 | Merzenich et al. ........... 345/619 |

OTHER PUBLICATIONS

Ball, KK, Beard, BL, Roenker, DL, Miller, RL, Griggs, DS. 1988. Age and visual search: Expanding the useful field of view. Optics, Image Science, and Vision, vol. 5: pp. 2210-2219.
Ball, K, Edwards, JD, Ross, LA. 2007. The impact of speed of processing training on cognitive and everyday functions. J Gerontology, vol. 62B: pp. 19-31.

(Continued)

*Primary Examiner* — Stephone B Allen
*Assistant Examiner* — Brandi Thomas
(74) *Attorney, Agent, or Firm* — McDermott Will & Emery LLP

(57) ABSTRACT

Cognitive deficits involving attention, sequential processing, reading, speed of processing, and navigation may be diagnosed and remediated in a subject by respectively measuring and improving contrast sensitivity for motion discrimination of the subject. A background may be displayed with a contrast and temporal frequency and either single, or multiple, higher spatial frequencies that may repeat over a wider area than the individual frequency components. A test window may be superimposed over the background, and includes a test pattern with a contrast and a spatial frequency and a temporal frequency. The subject may provide a signal indicative of the direction the subject believes the test pattern moved. In response to this signal, the contrast of the test pattern, the spatial frequency of the background, the spatial frequency of the test pattern, or the temporal frequency may be modified, either by increasing or decreasing its respective value.

17 Claims, 29 Drawing Sheets

(56) References Cited

OTHER PUBLICATIONS

Demb, JB, Boynton, GM, Heeger, DJ. 1998. Functional magnetic resonance imaging of early visual pathways in dyslexia. J. Neurosci. vol. 18: pp. 6939-6951.

Dennis, NA, Cabeza, R. 2008. Neuroimaging of healthy cognitive aging. In FIM Craik and TA Salthouse (Eds), The Handbook of Aging and Cognition. NY: Psychology Press, Ch. 1, pp. 1-54.

De Valois RL, Cottaris NP, Mahon LE, Elfar SD, Wilson JA. 2000. Spatial and temporal receptive fields of geniculate and cortical cells and directional selectivity. Vision Res, vol. 40: pp. 3685-3702.

Eden, GF, VanMeter, JW, Rumsey, JM, Maisog, JM, Woods, RP, Zeffiro, TA. 1996. Abnormal processing of visual motion in dyslexia revealed by functional brain imaging. Nature, vol. 382: pp. 66-69.

Fischer, B. Hartnegg, K, Mokler, A. 2000. Dynamic visual perception of dyslexic children, Perception, vol. 28: pp. 523-530.

Kaplan, E & Shapley, RM.1982. X and Y cells in the lateral geniculate nucleus of macaque monkeys. J. Physiology, vol. 330: pp. 125-143.

Lawton, T. 2004. Training directionally selective motion pathways can significantly improve reading efficiency, Human Vision and Electronic Imaging IX, Ed. B. E. Rogowitz and T.N. Pappas, Proc. of SPIE—IS&T Electronic Imaging, SPIE vol. 5292: pp. 34-45.

Lawton, T. 2007. Training Direction-Discrimination Sensitivity Remediates a Wide Spectrum of Reading Skills, Optometry and Vision Development, vol. 38: pp. 37-51.

Lawton, T. 2008. Filtered Text Improved Reading Fluency More Than Unfiltered or Colored Text Before and After Direction Discrimination Training for Both Dyslexic and Normal Readers, Optometry and Vision Development, vol. 39: pp. 114-126.

Lawton, T and Stephey, D. 2009. "Training direction discrimination improves usable field of view, short term memory, and navigation in older adults", Optometry and Vision Development, 40:2, 82-93.

Lehmkuhle, S. 1994. Neurological Basis of Visual Processes in Reading. In Willows, Corcos, and Kruk (Eds.), Visual Processes in Reading and Spelling, pp. 77-94. Mahwah, NJ: L. Erlbaum.

Livingstone, MS, Rosen, GD, Drislane, FW, Galaburda, AM. 1991. Physiological and anatomical evidence for a magnocellular defect in developmental dyslexia. Proceedings of the National Academy of Science, 88, 7943-7947.

Lovegrove, W.J., Bowling, A., Badcock, D., Blackwood, M. (1980) Specific reading disability: Differences in contrast sensitivity as a function of spatial frequency, Science, 210, 439-440.

Mapstone, M, Steffenella, TM, Duffy, CJ. 2003. A visuospatial variant of mild cognitive impairment: Getting lost between aging and AD. Neurology, vol. 60: pp. 802-808.

Maunsell, JH, Nealey, TA, De Priest, DD. 1990. Magnocellular and parvocellular contributions to responses in the middle temporal visual area (MT) of the macaque monkey. J Neurosci. vol. 10: pp. 3323-3334.

Nassi, JJ, Lyon, DC, Callaway, EM. 2006. The parvocellular LGN provides a robust disynaptic input to the visual motion area MT, Neuron, vol. 50, 2006: pp. 319-327.

Owsley, C, Sekuler, R, Siemsen, D. 1983. Contrast sensitivity throughout adulthood. Vision Res. vol. 23: pp. 689-699.

Owsley, C, Ball, K, Keeton, DM. 1995. Relationship between visual sensitivity and target localization in older adults. Vision Research, vol. 35: pp. 579-558.

Ridder, WH, Borsting, E, Banton, T. 2001. All developmental dyslexic subtypes display an elevated motion coherence threshold. Optometry and Visual Science, vol. 78: pp. 510-517.

Schefrin, BE, Tregear, SJ, Harvey, LO, Werner, JS. 1999. Senescent changes in scotopic contrast sensitivity. Vision Res. vol. 39: pp. 3728-3736.

Sclar, G., Maunsell, JHR, Lennie, P. 1990. Coding of image contrast in central visual pathways of the macaque monkey, Vision Res., vol. 30: pp. 1-10.

Stein, J. 2001.The magnocellular theory of developmental dyslexia. Dyslexia, vol. 7: pp. 12-36.

Stein, J and Walsh, V. 1997. To see but not to read; the magnocellular theory of dyslexia. TINS, vol. 20: pp. 147-152.

Talcott, JB, Witton, C, Hebb, GS, Stoodley, CJ, Westwood, EA, France, SJ, Hansen, PC, Stein, JF. 2002. On the relationship between dynamic visual and auditory processing and literacy skills; Results form a large primary-school study, Dyslexia, 8: pp. 204-225.

Temple E, Deutsch GK, Poldrack RA, Miller SL, Tallal P, Merzenich MM, Gabrieli JDE. 2003. Neural deficits in children with dyslexia ameliorated by behavioral remediation: Evidence from functional MRI, Proc Nat Acad Sci, vol. 100: pp. 2863-2865.

Trachentberg, JT and Stryker, MP. 2001.Rapid anatomical plasticity of horizontal connections in the developing visual cortex. Journal of Neuroscience, vol. 21: pp. 3476-3482.

Vidyasagar, TR. 1999. A neuronal model of attentional spotlight: parietal guiding the temporal. Brain Research Reviews, vol. 30: pp. 66-76.

Vidyasagar, TR. 2001. From attentional gating in macaque primary visual cortex to dyslexia in humans. In Progress in Brain Research. Eds. C. Casanova, M. Ptito, vol. 134: pp. 297-312.

Vidyasagar, TR and Pammer, K. 2009. Dyslexia: A deficit in visuospatial attention, not in phonological processing, Trends in Cognitive Sciences, vol. 14: pp. 57-63.

\* cited by examiner

Fig. 1. Sample patterns for test frequency = 0.5 cyc/deg (cpd) on Different Backgrounds

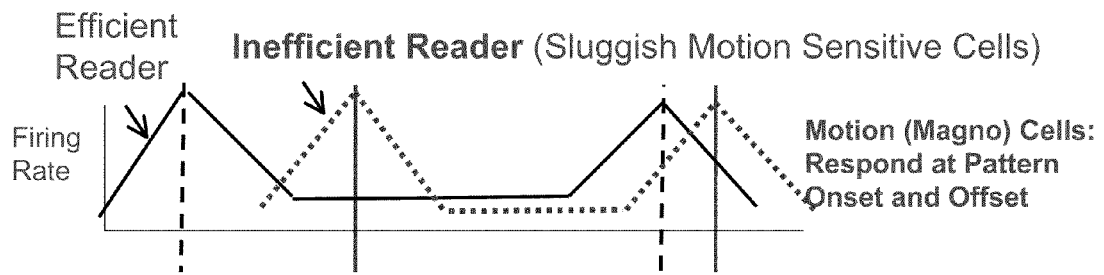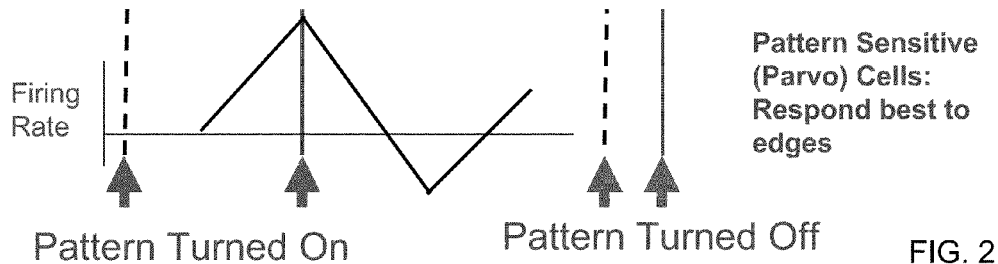
FIG. 2

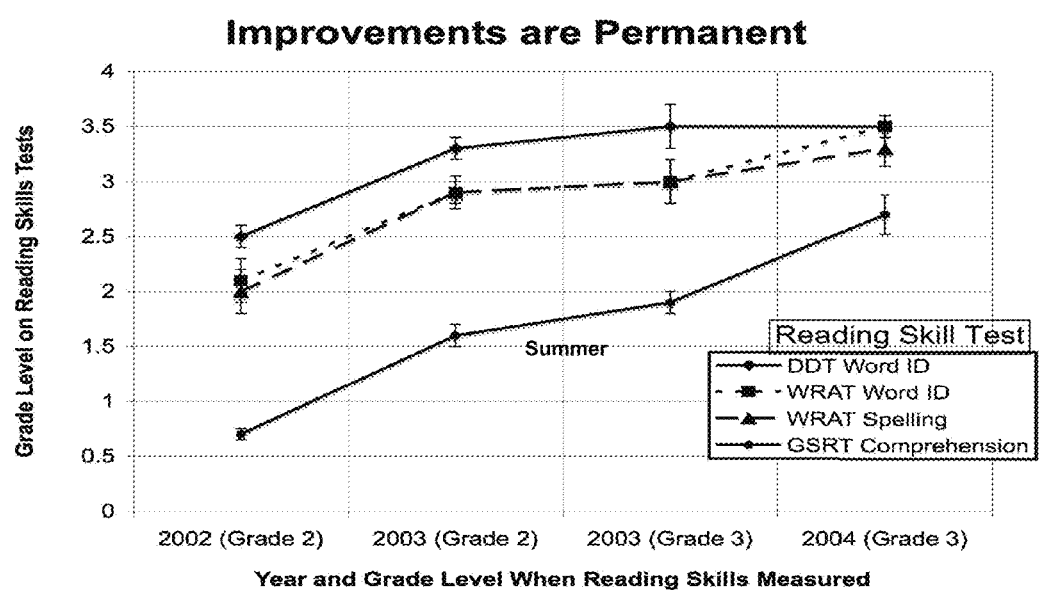
FIG. 12A. Improvements in Reading Skill tests (Dyslexia Determination Test (DDT), Wide Range Achievement Test (WRAT) Word Identification and Spelling subtests, Gray Silent Reading Test (GSRT)) from 2002 - 2004.

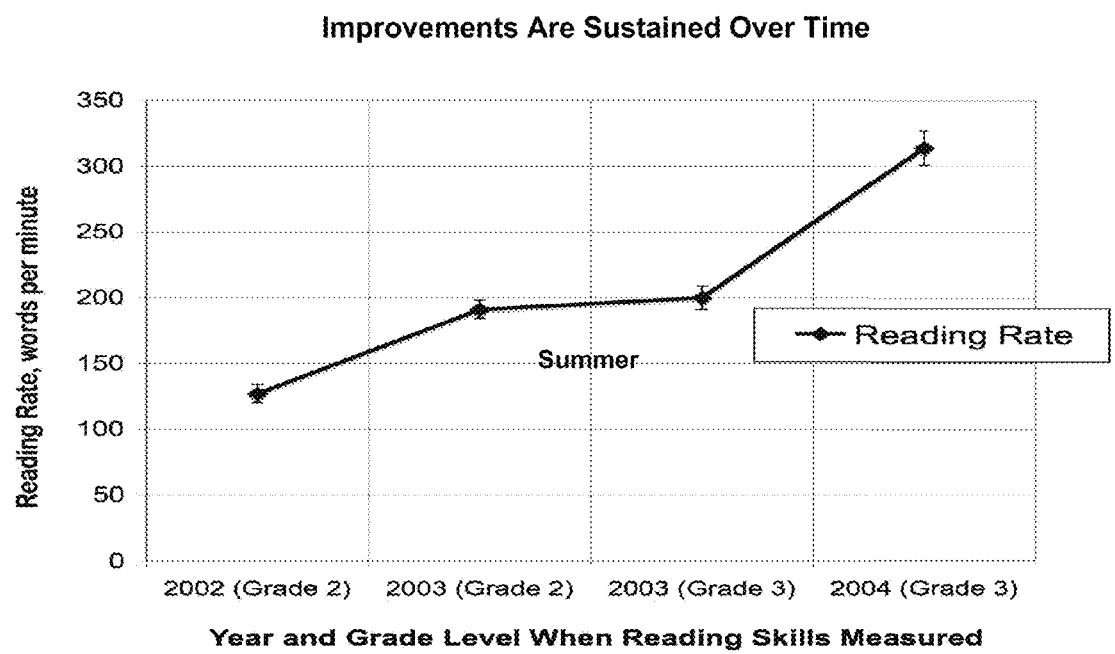
FIG. 12B. Improvements in Reading Rate from 2002 - 2004.

The Parameters for Each Level of Complexity:

| Complexity Level | Duration of Each Interval | Background Frequencies | Background Contrast |
|---|---|---|---|
| 1 | 150 msec | Single frequency | 5% |
| 2 | 150 msec | Multifrequency | 5% |
| 3 | 150 msec | Multifrequency | 10% |
| 4 | 150 msec | Multifrequency | 20% |
| 5 | 125 msec | Single frequency | 5% |
| 6 | 125 msec | Multifrequency | 5% |
| 7 | 125 msec | Multifrequency | 10% |
| 8 | 125 msec | Multifrequency | 20% |
| 9 | 100 msec | Single frequency | 5% |
| 10 | 100 msec | Multifrequency | 5% |
| 11 | 100 msec | Multifrequency | 10% |
| 12 | 100 msec | Multifrequency | 20% |
| 13 | 75 msec | Single frequency | 5% |
| 14 | 75 msec | Multifrequency | 5% |
| 15 | 75 msec | Multifrequency | 10% |
| 16 | 75 msec | Multifrequency | 20% |

FIG. 23

DIAGNOSING AND REMEDIATING COGNITIVE DEFICITS INVOLVING ATTENTION, SEQUENTIAL PROCESSING, READING, SPEED OF PROCESSING, AND NAVIGATION

CROSS-REFERENCE TO RELATED APPLICATIONS

This application is based upon and claims priority to U.S. Provisional Patent Application No. 61/166,997, entitled "Methods and Apparatus for Diagnosing and Remediating Cognitive Deficits Involving Attention, Sequential Processing, Reading, Speed of Processing, and Navigation," filed Apr. 6, 2009. This application is also related to U.S. Pat. No. 6,045,515, "Methods and Apparatus For Diagnosing and Remediating Reading Disorders". The entire content of this application and patent is incorporated herein by reference.

BACKGROUND

1. Technical Field

The present disclosure relates to diagnosing and treating cognitive deficits involving attention, sequential processing, reading, navigation, and speed of processing, deficits that occur naturally with age, and for treating reading disorders, such as dyslexia. More particularly, the present disclosure relates to methods and apparatus for measuring contrast sensitivity for motion discrimination at both high and low levels of cortical processing and to improving contrast sensitivity for motion discrimination.

2. Description of Related Art

When an image falls on the retina, it is processed within the retina to some extent. Retinal ganglion cells send signals out of the eye to a relay nucleus in the thalamus of the brain. Cells of the thalamus, in turn, send signals to the visual cortex for further processing. There are two major types of retinal ganglion cells, which respectively contact two classes of cells in the relay nucleus of the thalamus:

Parvocellular neurons and magnocellular neurons. Parvocellular neurons have small receptive fields and respond to visual tasks requiring a high degree of acuity.

Magnocellular neurons, which are about one-tenth as numerous as parvocellular neurons, have large receptive fields and respond to visual tasks requiring a high degree of movement sensitivity. They have coarse acuity and high contrast sensitivity.

In view of the above, the human visual system may be divided into two visual streams. The first is the dorsal stream, predominantly composed of magnocellular neurons, which detects movement. This dorsal stream has a high sensitivity to low contrast (for example, below 10%), to low luminance, to movement, and has low resolution. The second is the ventral stream, composed of both parvocellular and magnocellular neurons, which detects the color, shape, and texture of patterns. This second, or ventral, stream has low contrast sensitivity and high resolution. The ventral stream is most sensitive to contrasts above about 10%.

The parvocellular and magnocellular neurons, either alone or in combination, provide the information used by many different visual cortical pathways (or "streams"), which are specialized for performing different perceptual tasks. One such specialized pathway is a visual cortical area called Medial Temporal, or "MT", which is central to analyzing the direction of motion. Most of the signals that drive neurons in area MT derive from neurons in layer $4b$ of the primary visual cortex, V1, which, in turn, are primarily activated by input from the magnocellular cells (in humans, V1 is the only cortical area that receives signals from the retina via the thalamic relay nucleus.) Direction selectivity is a fundamental characteristic of magnocellular neurons in the dorsal stream, and is mediated by cells in both layer $4b$ and 6 of the primary visual cortex, V1, and in the MT cortex. In direction discrimination tasks, magnocellular neurons in the dorsal stream signal in advance of the linked parvocellular neurons in the ventral stream, which are sensitive to patterns. The timing and direction of visual events in the direction-selectivity network is signaled by magnocellular neurons, activated at pattern onset and offset. Detailed pattern information used to identify each word is signaled by parvocellular neurons, which provide the background frame of reference for judging the direction of movement.

If magnocellular neurons are a substrate of reading, then one would expect physiological and psychophysical plasticity in the neural channel's sensitivity to take place at the same time as functional changes in the cortical organization used for reading. Reading involves the coordination of saccadic eye movements, requiring the integration of information from the temporal and frontal lobes, and pattern recognition, requiring the integration of information from the occipital, temporal and parietal lobes. The temporal lobe shows peak synaptogenesis, i.e. developing and pruning synaptic contacts, at 6 to 10 years which corresponds with the time the child is learning to read. Moreover, both temporal and frontal cortical areas continue to develop into young adulthood. Experience refines the output of cortical circuits by introducing patterned activity that fine-tunes the strength of neuronal connections within and among cortical columns. Even in adulthood, brain plasticity results from a continuing process of experience-dependent synaptogenesis. Perhaps, during a time of peak developmental plasticity, as when the child is learning to read, the cortical neuronal connections are especially plastic. Direction discrimination is still developing in young children.

Certain aspects of the magnocellular networks, such as direction discrimination and the ability to detect brief patterns are still developing in 5 to 9 year old children as compared to normal adults, so children aged 5 to 9 years, both normal and dyslexic, benefit from training to improve motion discrimination. Moreover, there is increasing psychophysical, physiological, and anatomical evidence that dyslexics have anomalies in their magnocellular networks manifested by (1) higher contrast thresholds to detect brief patterns, (2) an impaired ability to discriminate both the direction and the speed of moving patterns, and (3) unstable binocular control and depth localization when compared to age-matched normals. The lack of synchronization in timing between magnocellular and parvocellular activations, caused by sluggish magnocellular neurons, may be what has been disrupted in dyslexia, shown schematically in FIG. 2, resulting in temporal and spatial sequencing deficits that slow reading speeds and processing speed. The dyslexic reader's more sluggish, magnocellular neurons may cause a deficit in attentional focus, preventing the linked parvocellular neurons from isolating and sequentially processing the relevant information needed when reading.

In older adults, timing deficits manifest themselves as an impaired ability to pay attention, navigate, perform figure/ground discrimination, and process information sequentially and quickly. Processing speed deficits may underlie the cognitive decline found in older adults; the prevalence of these deficits increases with age. There is functional Magnetic Resonance Imaging (fMRI) evidence that, just like is found for dyslexics, cortical areas V1 and MT in older adults show less activation than do those areas in younger adults. In addition, older adults have a decreased sensitivity to radial motion, i.e. optic flow, analyzed in cortical area MST, that is directly related to impaired navigational skills. Moreover, behavioral data show that adults over 50 have decreased contrast sensitivity to stationary and moving sine wave gratings at low spatial frequencies under all viewing conditions. These contrast sensitivity losses may be due to age-related changes in magnocellular pathways.

Recent fMRI studies indicate that older adults exhibit more dorsal prefrontal activation when performing tasks than their younger counterparts as a result of needing to expend more processing effort. This is consistent with a degradation of magnocellular pathway timing. Reduced information processing speed, resulting from sluggish magnocellular neurons, may explain problems in memory encoding and retrieval because this mental slowing can lead to superficial processing and inefficient strategies where elaboration is required.

For older adults, training regimens employing motion detection and discrimination combined with object recognition improved processing speed, functional field of view, and performance in driving and other mobility and navigation tasks. These training regimens present high contrast patterns that are not as effective in improving cognitive deficits, as found when using low contrast grayscale patterns for direction discrimination training. Moreover, none of these training regimens improved the contrast sensitivity for motion discrimination, which is directly related to the amount reading speed, or processing speed, improved. Since the output of neurons in the visual cortex is directly related to pattern contrast, and stimulus contrast modulates cortical functional connectivity, high contrast patterns are not able to train the motion or dorsal stream, and instead train the ventral stream. Other methods to improve processing speed present patterns with such rapidity that they are not of sufficient duration and of low enough contrast to train magnocellular neurons at the anterior portion of the dorsal stream. Cognitive therapies, like remembering a sequence of letters and/or digits, are designed to activate the ventral and not the dorsal stream. Conventional wisdom in the art, e.g. the Mayo clinic, teaches that either doing nothing but monitoring the patient or providing medications that have not yet been shown to be effective in treating mild cognitive impairments are used to manage age-related cognitive impairments. Therefore, none of these interventions may improve cognitive impairments as efficiently or effectively as done by training direction discrimination between patterns that optimally activate magnocellular neurons.

A natural assumption in the art is that reading relies on the high-resolution acuity system, which may be evaluated by measuring visual acuity using the familiar Snellen index (20/20, 20/40, and so on as known in the art). Conventional wisdom in the art teaches that dyslexia, which may be defined as a reading deficit in a child of normal intelligence and an adult-level acuity (i.e. 20/20), is a difficulty in decoding or encoding words on a page that are readily seen. Most reading therapies concentrate on improving phonological awareness instead of improving processing in the motion-sensitive dorsal stream, as occurs with direction discrimination training, the invention being disclosed. Vision-based reading therapies, integrated with phonological training, work with high contrast patterns that are aimed at improving processing in the ventral stream (identifying the letters in a word and the words on a page) and not the dorsal stream.

Motion sensitive (magnocellular) sensitive neurons must be activated to remediate the underlying direction discrimination deficit in the dorsal stream. The posterior portion of the dorsal stream is trained, when using the original invention, to be more sensitive and respond more quickly to discriminating the direction of movement. Others claim that the posterior portion of the cortex is not able to be trained to improve reading, and these assumptions have now been proven to be false, since direction discrimination training using patterns that activate magnocellular neurons significantly improved reading fluency. Moreover, differences between children with reading problems (e.g. those who are dyslexic) and children with normal reading skills were revealed only by tests focusing on the cortical movement system. Tests focusing on the pattern system, such as assessing visual acuity or word recognition using long duration patterns, were unable to discriminate between children with normal reading skills and children with reading problems. Furthermore, no other vision therapy has been found to improve phonological deficits, suggesting that improving the timing in the brain may be the foundation needed to improve a wide range of reading deficits (both visual and phonological) and cognitive deficits, including attention, figure/ground discrimination, sequential processing, speed of processing, navigation, and visual memory.

The motion contrast sensitivity training that has thus far been provided, however, may fail to: 1) incorporate larger numbers of differing neural channels at each level of cognitive processing, and 2) train motion discrimination at higher levels of cognitive processing in the dorsal stream, sharpening the attention gateway, so figure/ground discrimination, sequential processing, visual memory, and navigation can be done effortlessly. Tasks at higher levels in the dorsal stream, most notably in the dorsal lateral prefrontal cortex where sequential processing, executive control of attention, and visual working memory are computed, are trained by remembering a sequence of patterns. There may be no intervention available that uses patterns that maximally activate magnocellular neurons to train a person to remember a sequence of patterns. Therefore, there may be no interventions to improve cognitive processing in the anterior portion of the dorsal stream.

SUMMARY

One objective is to diagnose and remediate a wide range of cognitive disorders by respectively measuring and improving a subject's contrast sensitivity for motion discrimination using a bottom-up training method, which activates subsequently higher levels of cortical processing in the dorsal stream, improving the timing of magnocellular relative to parvocellular activations so that attentive processing can be done with little effort. Dyslexic children who practice the methods of the present disclosure may increase their reading rates an average 11 fold. There may also be a marked increase in reading rates in children with previously determined normal ability. Moreover, the contrast sensitivity for motion discrimination of children with dyslexia may improve 4-12 fold and the cognitive abilities of older adults who have trouble with figure/ground discrimination, navigation, working visual memory, sequential processing, and attention may improve remarkably after a short amount of training (e.g., twice a week for 10 minutes over 12 weeks). By improving the magnocellular timing in the brain using the present disclosure, the speed of processing may increase, improving the attention gateway and the functional field of view.

In one embodiment, a background is displayed on a monitor at a level of contrast, one or several spatial frequencies, and is either stationary or moving at the same speed, and in the same or a different direction than the test pattern, which is in a test window superimposed over the background. The test window contains a test pattern at a prescribed level of contrast with both a spatial frequency and a temporal frequency. The test pattern is then moved within the test window. Low-complexity (single frequency) backgrounds are used initially until low contrast thresholds for discriminating the direction of movement are reached for a range of different patterns. The next level of complexity is then chosen automatically by the computer, which first increases the background from single to multiple frequencies, then increases background contrast, and finally increases temporal frequency. This increase in complexity involves increasing contrast from 5% to 20%, and temporal frequency from 6.7 cycles per second (Hz) up 13.3 Hz, which is centered around the subject's peak temporal frequency of 10 Hz, so the task is challenging but not too difficult. The contrasts and the spatial and temporal frequencies are within respective ranges that stimulate the visual cortical movement system, i.e. the dorsal stream. The subject provides a signal indicative of the direction the subject believes the test pattern moved in one or more intervals, e.g. with two or more intervals being used to test and train attention, sequential processing, and visual working memory. In response to this signal: 1) the contrast of the test pattern; 2) the contrast, spatial or temporal frequency, or the direction of movement of the background relative to the test pattern; 3) the number of pattern intervals, and/or the spatial or temporal frequency of the test pattern, are modified by the computer, either by increasing or decreasing their respective values. This process may then be repeated a number of times, cycling through predetermined combinations of test patterns and backgrounds. Contrast sensitivity may be measured to determine whether a child is dyslexic or an older adult has diminished speed of processing. Repeated stimulation by what is disclosed may improve contrast sensitivity for motion discrimination, which improves magnocellular timing. When followed by practice on reading and other cognitive tasks, what is disclosed may: 1) remediate dyslexia and other cognitive deficits, 2) improve ability to pay attention, navigate, perform figure/ground discrimination, 3) increase speed of processing, 4) increase functional field of view, and/or 5) improve the ability to process information sequentially and rapidly, and read more quickly with better comprehension. Once the initial program with all levels of complexity is mastered for moving test patterns against a stationary background, which may tap into the lowest levels of the dorsal stream, subsequent training may involve moving test patterns against moving backgrounds, first moving the same direction, and then in a different direction from the test pattern. These tasks may tap into higher levels in the dorsal stream. Once these two programs are mastered at all levels of complexity, widening the functional field of view and improving speed of processing even more, then a sequence of discrete movements may be displayed to test and train the anterior portion of the dorsal stream, the highest level in the dorsal stream. These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

FIG. 2 is a schematic view showing how temporally-based activity of magnocellular neurons (changes over time) brackets the spatially-based activity of parvocellular neurons (relative to changes across space) for efficient readers, and the lack of bracketing for dyslexics. The magnocellular neurons fire at pattern onset and offset, whereas the parvocellular neurons transmit the varying contrast over space, i.e. the edge information. This model illustrates how sluggish magnocellular neurons may prevent sequential processing from being done accurately.

FIG. 12A is a graphical view of data illustrating relationships between grade level improvements of reading skills before and after direction discrimination training for dyslexic subjects who were trained for two consecutive years in their school classrooms.

FIG. 12B is a graphical view of data illustrating relationships between improvements in reading speed before and after direction discrimination for dyslexic subjects who were trained for two consecutive years in their school classrooms.

FIG. 23 is a tabular view of the parameters used to determine the 16 levels of complexity for the direction discrimination training, each level increasing the level of processing in the cortical hierarchy in the dorsal stream.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Figure 24:
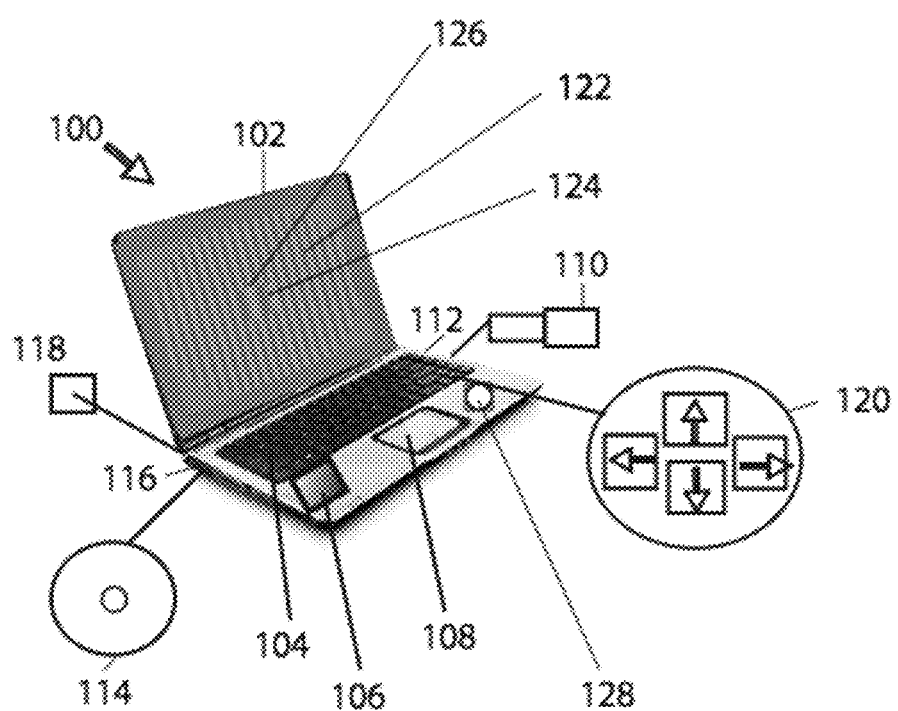
FIG. 24 is a perspective view of a computer system configured in accordance with an exemplary embodiment of the present disclosure for measuring and improving contrast sensitivity for motion discrimination.

Referring more particularly to the drawings, an exemplary computer system for measuring improving the contrast sensitivity for motion discrimination of a subject and configured in accordance with the teachings of the present disclosure is illustrated in FIG. 24 as a computer system.

This exemplary computer system embodiment may be configured to measure and also improve a subject's contrast sensitivity for motion discrimination in the dorsal stream of the visual system at both low levels, as done in the previous invention, and high levels, as done in the present disclosure. Contrast sensitivity measurements may be used to determine whether a subject suffers from a neural timing disorder that directly affects the speed and effectiveness of brain processing, such as a reading or cognitive disorder involved in impairments like dyslexia, attention deficit disorder, amblyopia, autism, schizophrenia, Traumatic Brain Injury (TBI), and aging.

The present disclosure may activate and train higher levels of cognitive processing in the dorsal stream by improving the timing of motion sensitive neurons, thereby: 1) broadening the attention gateway to improve speed of processing, and 2) improving brain functioning in more complex cognitive tasks, involving figure/ground discrimination, visual memory, sequential processing, and navigation. Improving contrast sensitivity for motion discrimination results in an improvement in reading and cognitive abilities and a remediation of the reading and/or cognitive disorder. In other words, the present disclosure may be used to cure dyslexia, problems in reading skills, as well as cognitive disorders associated with aging, and traumatic brain injuries. For purposes of this description and without limiting the scope of the present disclosure, an exemplary embodiment may include a computer 100, which is connected to output devices such as a display 102, and speaker 106 or other sound-producing device. Computer 100 may also be connected to input devices such as a keyboard 104, a mouse 108, and/or a microphone 128, as illustrated in FIG. 24.

Exemplary methodology of the present disclosure may be implemented on the system in the form of instructions stored as computer-readable code, which configures the exemplary computer 100 to perform in accordance with the present disclosure. These instructions may be stored on computer-readable storage medium such as a compact disc read-only memory (CD-ROM), or a digital video disk (DVD) 114 or a flash memory stick 110 for downloading into a computer through a CD-ROM/DVD drive 116 or a USB drive 112, respectively. Alternatively, the computer instructions may be downloaded into a computer 100 through an Internet connection 118 as known in the art. In addition, the computer 100 may include a hard disc on which computer-readable instructions may be pre-stored or "bundled" as known in the art. The exemplary computer system 100 may be configured as an IPC SPARCstation manufactured by Sun Microsystems, including a high-resolution monitor and a high speed computer, a Macintosh computer, or a Windows or Vista based personal computer which may provide high-speed with high-resolution monitors at a relatively low cost.

Definitions. The following definitions apply, unless otherwise indicated:

Contrast: the ratio of the difference between the luminance of the lightest and darkest portion of a pattern, divided by the sum of the luminance of the lightest and darkest portion of the pattern.

Contrast threshold: the lowest contrast of a moving test pattern which a subject can correctly identify the direction of motion of the moving test pattern a high percentage of times, such as 79%, of the times.

Contrast sensitivity: the inverse of the contrast threshold.

Spatial frequency: the number of times a pattern repeats itself within one degree of visual angle, which, in the case of a sinewave grating, is the number of times one bright and one dark bar repeats within one degree of visual angle.

Single spatial frequency: the spatial frequency of a pattern which repeats itself at the same rate.

Figure 3:
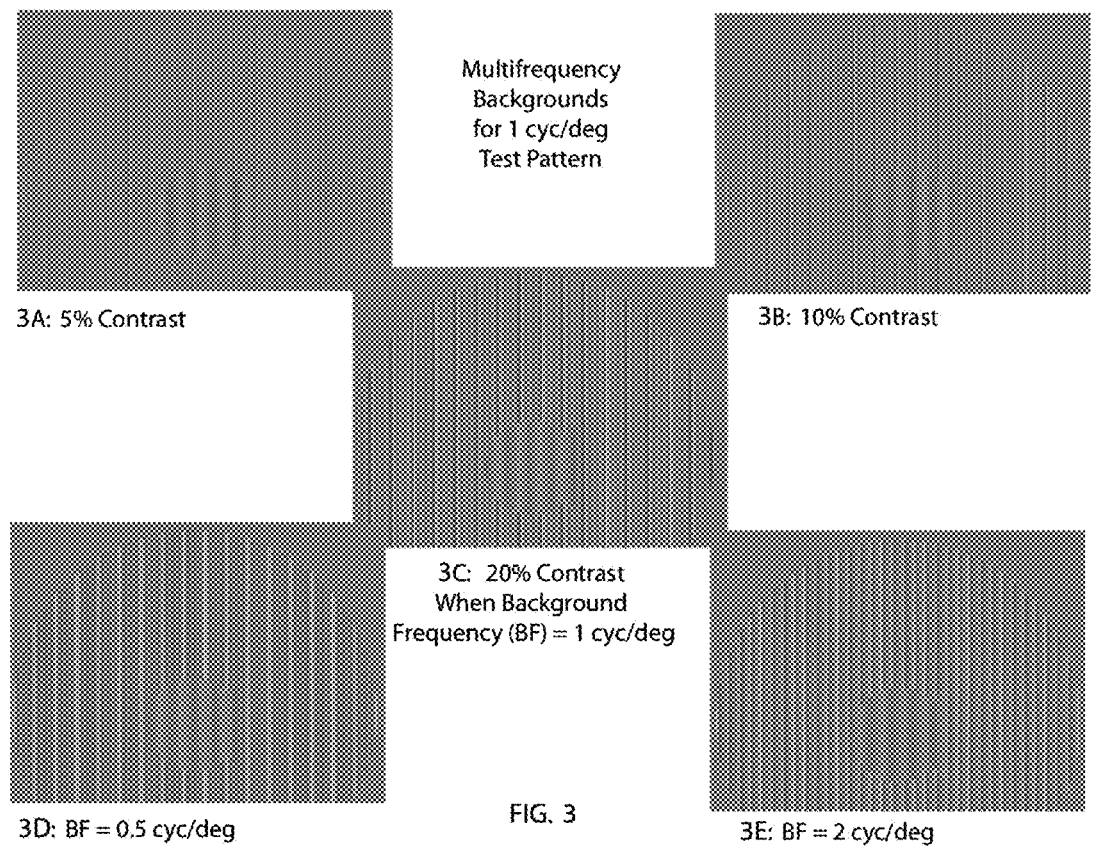
FIG. 3 is a view of exemplary visual stimuli displayed in accordance with the present disclosure, particularly illustrating a test window with a test pattern superimposed over a background at the second through fourth level of complexity where the multifrequency background increases in contrast from 5%, 10% and 20%, and where the multifrequency background increases from a fundamental frequency one octave below the spatial frequency of the test pattern (0.5 cycle per degree), equal to the test pattern (1 cycle per degree), or one octave above the spatial frequency of the test pattern (2 cycles per degree), respectively, particularly illustrating the relationship at a spatial frequency of 1 cycle per degree of the test pattern.

Multiple Spatial Frequencies: the spatial frequencies of a pattern which repeats itself at different rates (examples are shown in FIG. 3). Multiple spatial frequencies may be generated by combining the luminances of several single spatial frequency gratings together in cosine phase.

Octave: A doubling or halving in spatial frequency is one octave.

Harmonically-Related Frequencies: Frequencies that are a harmonic of a base frequency. Spatial frequency components may be harmonically-related to the frequency of a test pattern (e.g., test pattern 124) so that, when combined, they repeat over an area equal to or wider than the spatial width of one cycle of the spatial frequency of the test pattern. In one embodiment, this may be done by starting with the original background's spatial frequency that is either four times wider than the test spatial frequency (2 octaves lower), twice as wide (one octave lower), equal to, twice as narrow (1 octave higher), or four times narrower (2 octaves higher) than the test spatial frequency, and then adding in higher spatial frequencies having a difference frequency equal to the test frequency, lowering the fundamental frequency for background spatial frequencies higher than the test frequency, and not changing the fundamental frequency of the background frequencies lower than the test frequency. For example, the single frequency background of 2 cyc/deg generates a multiple spatial frequency of 2+3+4 cyc/deg when the test pattern is 1 cyc/deg, see FIG. 3E, which has a fundamental frequency of 1 cyc/deg, instead of 2 cyc/deg, as is the case for the corresponding single frequency background, shown in FIG. 1E.

Temporal frequency: the rate at which a pattern moves. For example, in apparent movement, where stationary patterns are shown in rapid succession, with only the spatial position of the pattern changing in successive frames, the test pattern may move every 150 msec, yielding a temporal frequency of 1000/150=6.7 cycles per second or 6.7 Hz.

Figure 25:
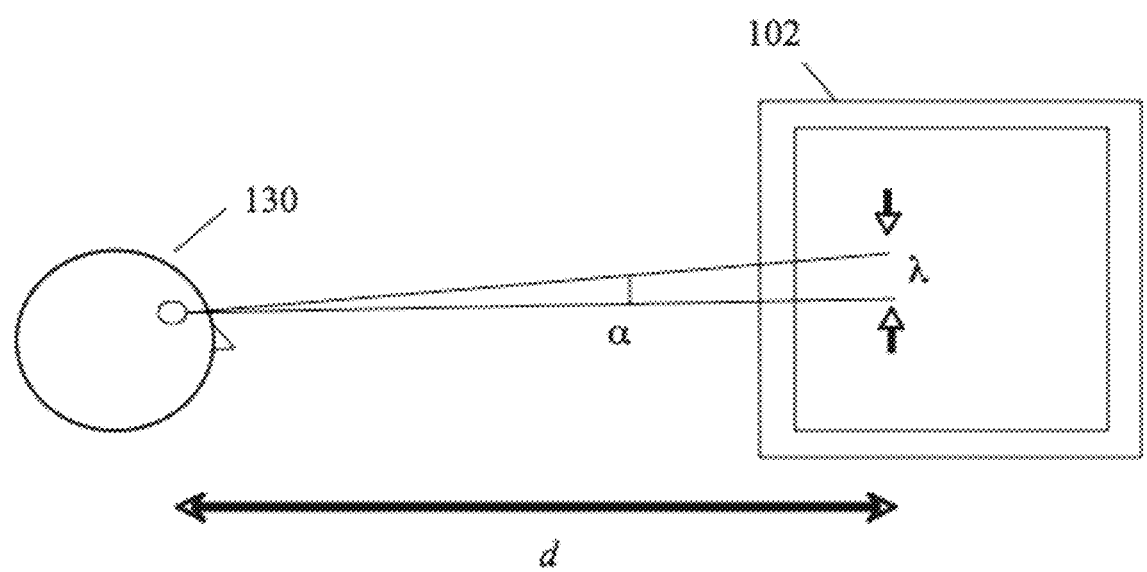
FIG. 25 is a schematic view of a subject and a monitor of the computer system of the disclosure, illustrating principles of visual angle.

Visual Angle: the angle subtended on the back of the eye by a pattern. In reference to FIG. 25, a subject 130 of whom contrast sensitivity for motion discrimination is to be measured is positioned a distance d from the monitor 102. A visual angle α accordingly exists between the subject 130 and the monitor 102, shown in FIG. 25. In accordance with the present disclosure, the subject 130 is positioned with respect to the monitor 102 such that visual angle α is defined to be 1 degree for about every 1 centimeter (cm) of arc length λ. To yield such a relationship between visual angle α and arc length λ, the subject 130 is positioned about 57 cm from the monitor 102 (i.e. the distance d is about 57 cm from the monitor 102).

To discuss the spatial frequencies of the background 122 and the test pattern 124 in more detail, reference is made to FIG. 24. The respective spatial frequencies at which background 122 and test pattern 124 are displayed may be defined as the rates at which the respective stripes repeat. In this regard, the respective spatial frequencies at which the background 122 and the test pattern 124 are displayed are measured in cycles per degree (of visual angle). For example, if the spatial frequency of the test pattern 124 is 1 cycle per deg (cyc/deg), then there would be one light stripe and one dark stripe for about every 1 cm on the monitor 102 when the subject 130 is positioned about 57 cm away. As shown in FIG. 1d, the background 122 is being displayed at about 1 cyc/deg while the test pattern 124 is being displayed at about 0.5 cyc/deg.

Figure 1:
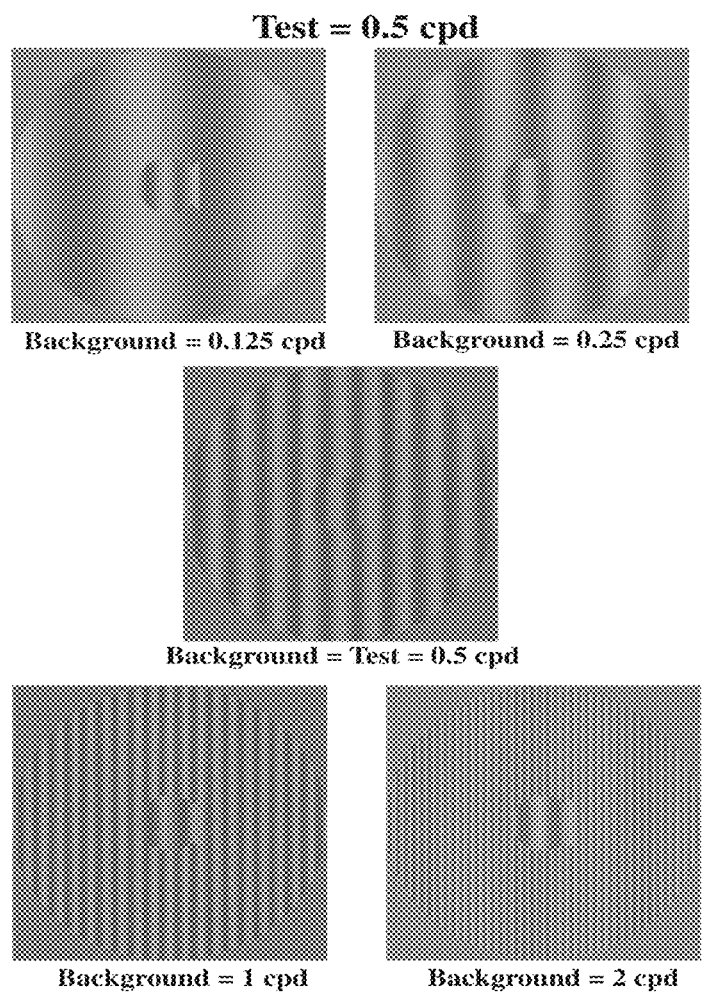
FIG. 1 is a view of exemplary visual stimuli displayed in accordance with the previous invention, U.S. Pat. No. 6,045,515, particularly illustrating a test window with a test pattern superimposed over a background at the first level of complexity in accordance with the present disclosure, and particularly illustrating the relationship at a spatial frequency of 0.5 cycle per degree of the test pattern.

Briefly, referring to FIG. 24, the exemplary computer 100 is configured to display on a monitor 102 visual stimuli in the form of a background 122 and a test pattern 124. The test pattern is displayed within a test window 126, which is superimposed over the background. Both the background and the test pattern are displayed at a contrast level (e.g. 5%) and at a spatial frequency (e.g. 1 cyc/deg) and temporal frequency (e.g. 10 Hz). As illustrated in FIG. 1, exemplary background and test patterns may be displayed as a plurality of light and dark vertical stripes which alternate in a substantially sinusoidal manner. Alternative, the stripes may be at any orientation. Other terminology describing the stripes may be sine wave gratings.

To discuss the respective contrasts at which the background 122 and the test pattern 124 are displayed, reference is made to FIG. 3. Accordingly, a contrast of 5% indicated that the brightest portion of the light stripes (i.e. the peak) are 5% lighter than the average gray level, and that the darkest portion of the dark stripes (i.e. the troughs) are 5% darker than the average gray level.

Exemplary background 122 and test pattern 124 have a spatial relationship with respect to each other in that the background is substantially larger than the test pattern, for example, on the order of about 5 times larger. In terms of the visual angle, the background 122 may be displayed on the monitor 102 to subtend about 20 degrees of visual angle, while the test pattern 124 may be displayed to subtend about 4 degrees of visual angle. The test window 122 is preferably centered within the background 122 and in the form of a familiar shape for children, for example, a fish. Generally speaking, exemplary test window 126 is substantially circular.

The contrast at which the background 122 is displayed and the contrast at which the test pattern 124 is displayed are selected from a predetermined range of contrasts which stimulate the visual cortical movement system of the subject 130. As known, the visual cortical movement system of humans includes the magnocellular neurons as described above and is selectively stimulated by contrasts which are less than about 10%. In accordance with the present disclosure, exemplary background 122 is displayed with a contrast of about 5% for the first level of complexity, as displayed in FIG. 1 and FIG. 3a. The contrast of the background increases at higher levels of complexity, e.g. see FIG. 3B where the background has a 10% contrast, and FIGS. 3C, 3D, and 3E where the background has a 20% contrast to increase the interactions between magnocellular and parvocellular neurons. Exemplary test pattern 124 is displayed at a contrast ranging from 0% to 10% using a double staircase method to determine the contrast threshold value that enables the subject to discriminate the direction of movement correctly 79% of the time in an exemplary embodiment. The contrast threshold value can also be determined for 70% correct responses; in fact, it can be a wide range of values, as long as it is well above 50%, chance, and below 100%.

The spatial frequency at which the background 122 is displayed and the spatial frequency at which the test pattern 124 is displayed are selected from a predetermined range of spatial frequencies which stimulate the visual cortical movement system of the subject 130. In accordance with the present disclosure, the spatial frequency at which exemplary test pattern 124 is displayed is less than about 5 cyc/deg. And the spatial frequency at which exemplary background 122 is displayed is equal to or a few octaves higher or a few octaves lower than the spatial frequency of the test pattern; in other words, the background spatial frequency is centered about the test-pattern spatial frequency, see FIG. 1.

Figure 7:
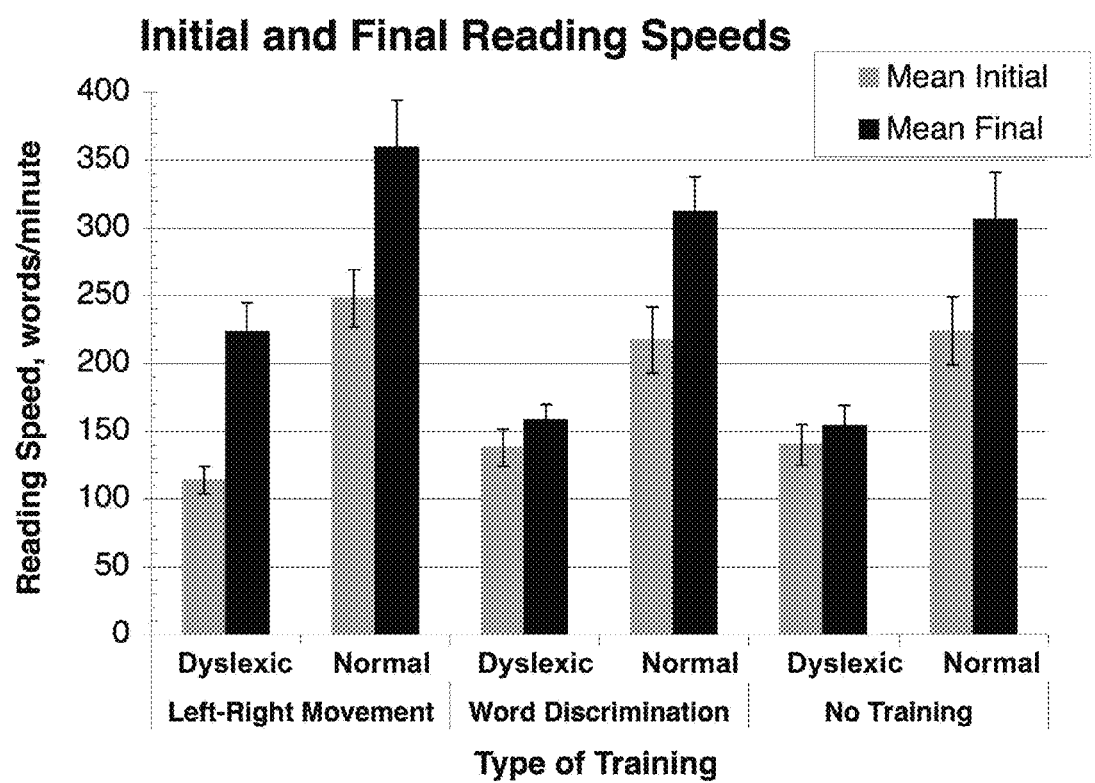
FIG. 7 is a graphical view of data illustrating relationships between reading rates with respect to different training regimens for dyslexic and normal subjects.
Figure 13:
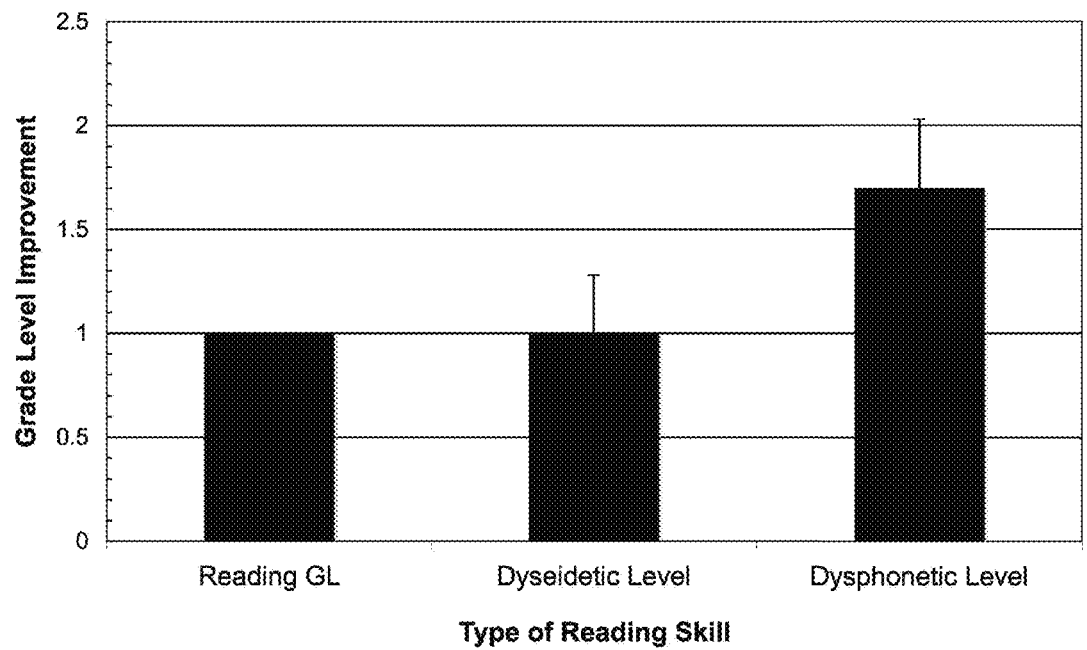
FIG. 13 is a graphical view of data illustrating relationships between reading skills following left-right movement discrimination training for dyslexic subjects.
Figure 14:
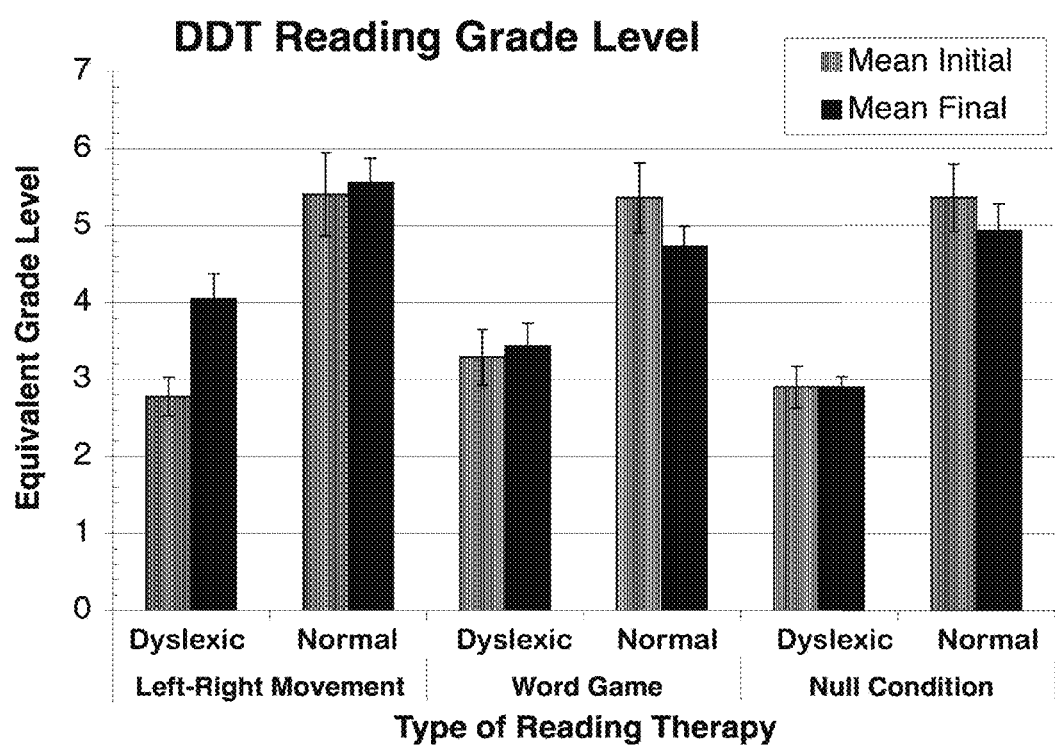
FIG. 14 is a graphical view of data illustrating relationships between reading grade level of word identification skills, measured by the Dyslexia Determination Test (DDT) with respect to different training regimens for dyslexic and normal subjects.
Figure 15:
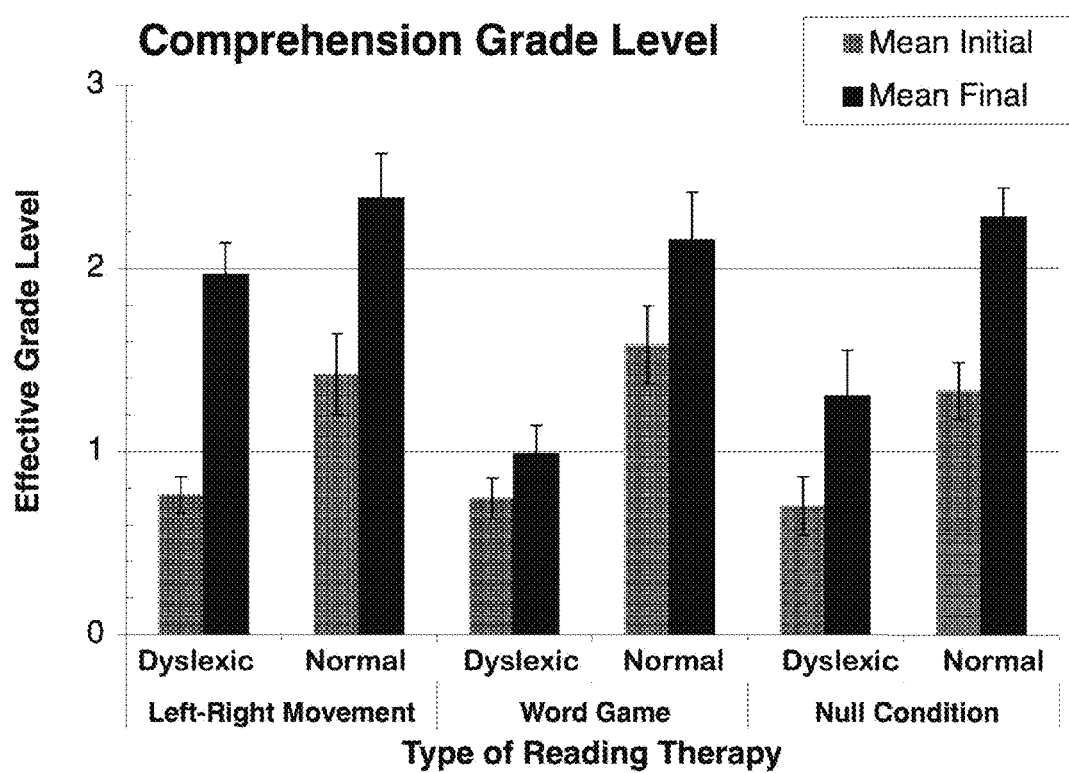
FIG. 15 is a graphical view of data illustrating relationships between reading comprehension skills with respect to different training regimens for dyslexic and normal subjects.
Figure 16:
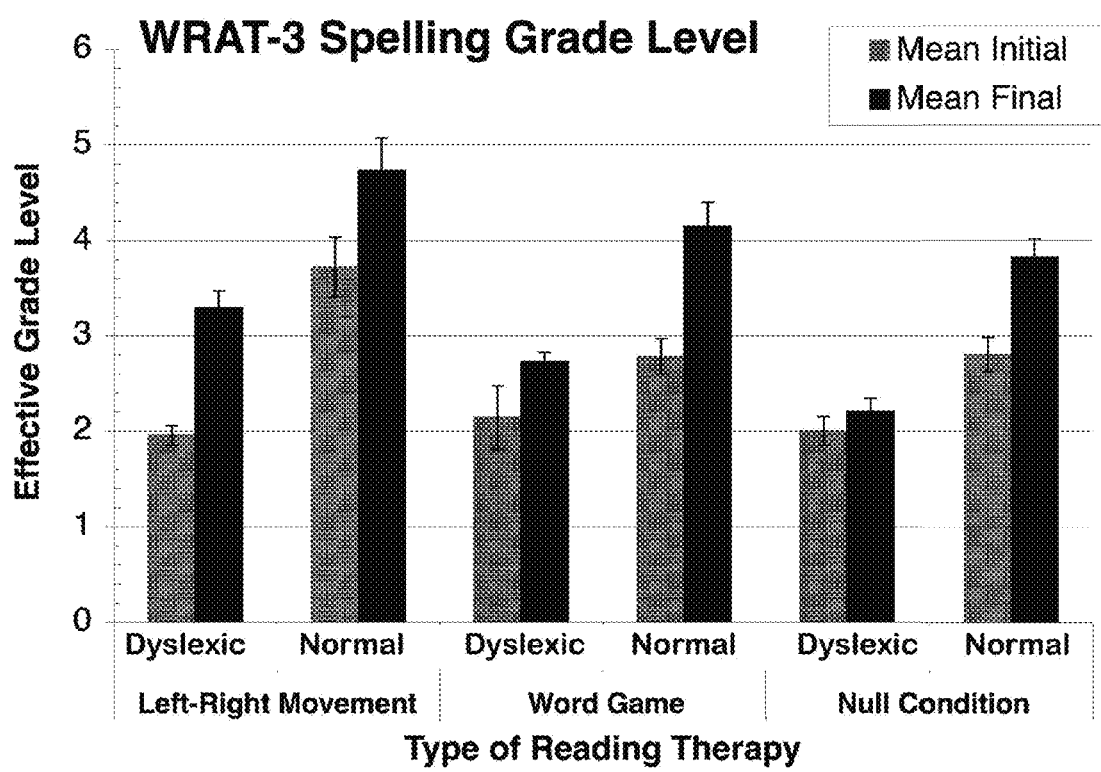
FIG. 16 is a graphical view of data illustrating relationships between grade level of spelling skills, measured by Wide Range Achievement Spelling (WRAT-3) subtask with respect to different training regimens for dyslexic and normal subjects.

The exact terminology for describing the stimulus parameters, such as contrast, spatial frequency and temporal frequency of the sine wave gratings used to generate the test and background patterns are described above. The present disclosure may include additional stimulus parameters, at higher levels of complexity than the one level patented previously, including multifrequency backgrounds at contrasts from 5% up to 20% (FIGS. 3A-C), having a fundamental spatial frequency that is lower (FIG. 3D) or equal to the test frequency (FIGS. 3C, 3E), and increasingly faster presentations than those used in the original invention, from 6.7 Hz up to 13.3 Hz. These changes improved reading speeds for dyslexic children even more, 4-fold on average when 8 levels of complexity were used, 11 fold on average when 16 levels of complexity were used (see FIGS. 8-11) rather than the 2-fold average improvements in reading rates, as shown in FIG. 7, when only one level of complexity was used, as illustrated in FIG. 1. Using 8 levels of complexity also increased the reading rates of normal children significantly more than when one level of complexity was used. Moreover, these changes were sustained over time (FIG. 12), and kept improving the more often the present disclosure was used, as shown in FIGS. 8-12, and 18. When 16 levels of complexity, exemplary levels listed in FIG. 23, were used to train motion discrimination, children improved one grade level in decoding and encoding skills, in addition to reading grade level, as shown in FIG. 13. Not only did reading speed, decoding and encoding words improve, as shown in FIGS. 7-14, but after being trained on one level of complexity, reading comprehension and spelling also improved as shown in FIGS. 15, 16.

Figure 17:
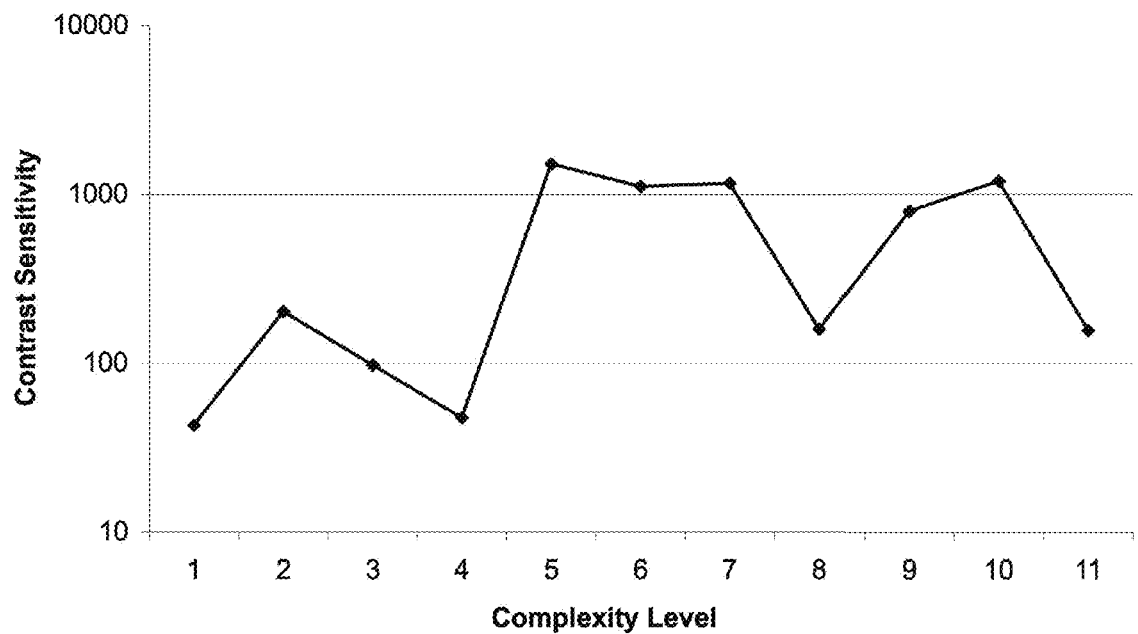
FIG. 17 is a graphical view of data illustrating relationships between contrast sensitivity for direction discrimination on each level of complexity for one subject who was amblyopic, particularly illustrating the relationship at a spatial frequency of 1 cycle per degree of the test pattern, when data were averaged across each of the 5 background frequencies.
Figure 18:
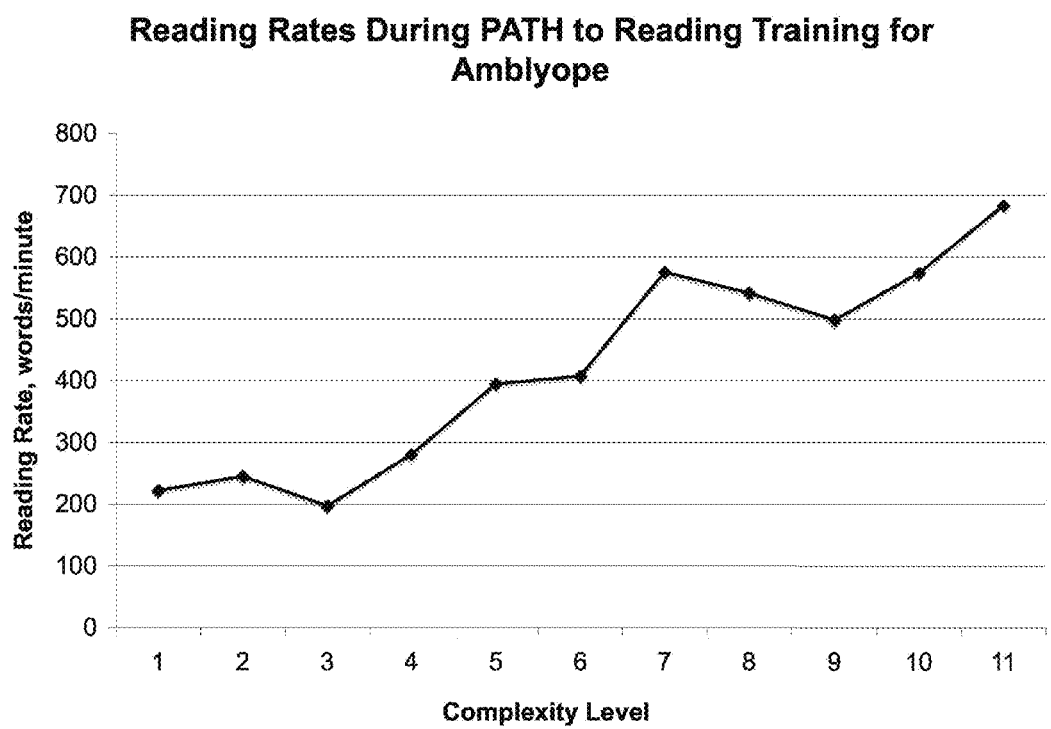
FIG. 18 is a graphical view of data illustrating relationships between reading rates following direction discrimination training at each level of complexity for one subject who was amblyopic.
Figure 19:
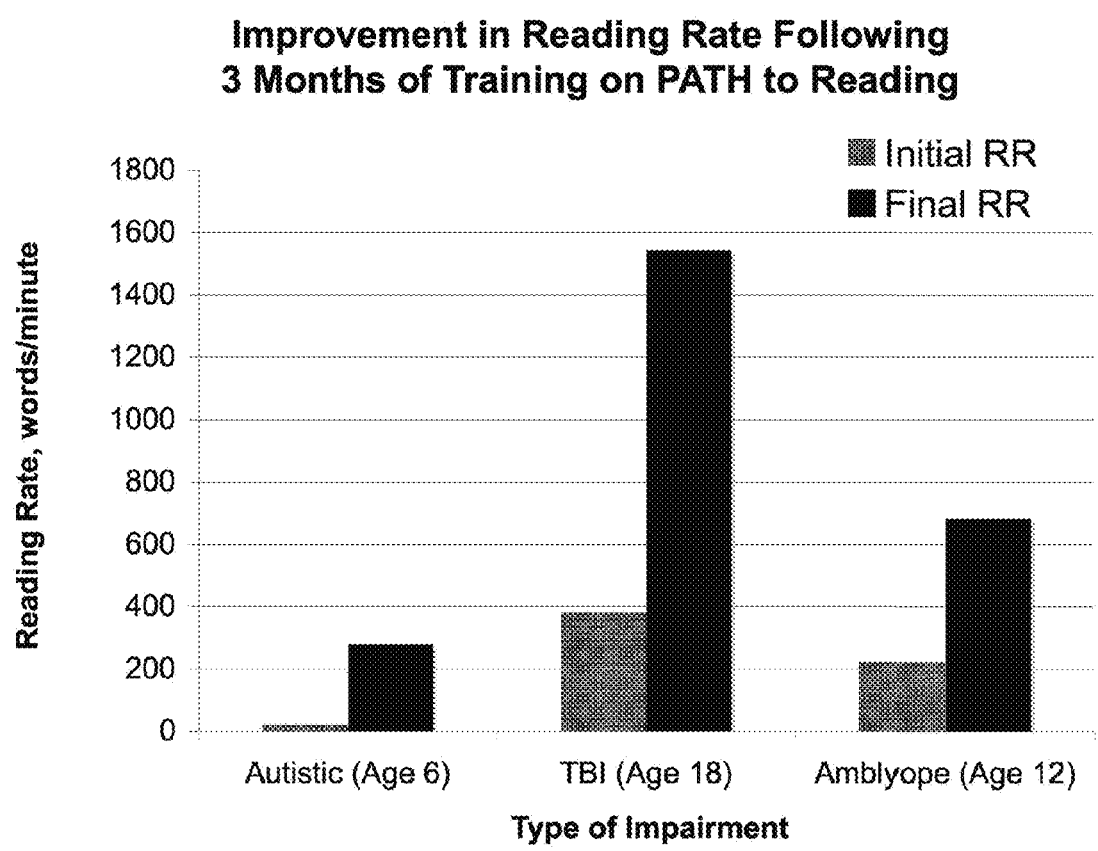
FIG. 19 is a graphical view of data illustrating relationships between reading rates before and after direction discrimination training at each level of complexity for three subjects, one was autistic, one had traumatic brain injury (TBI) and one was the amblyope of FIGS. 17 and 18.

Using 16 levels of complexity also increased both the contrast sensitivity and reading speed of a child with amblyopia, as shown in FIGS. 17 and 18, as well as for children with autism and Traumatic Brain Injury (TBI) as shown in FIG. 19. In addition, using 16 levels of complexity also increased both the contrast sensitivity of older adults, FIGS. 20a-d and 21, and their cognitive impairments. After the first month of training, all older subjects reported they noticed significant improvements in their field of usable vision, figure-ground discrimination, working memory, and navigation, especially at night. In addition, these tasks now required much less conscious effort. Improving motion discrimination contrast sensitivity through training using the present disclosure improved neural timing so that speed of processing improved for all older subjects. Moreover, for these older subjects, none of these improvements have regressed over time.

In addition to varying the stimulus parameters used for training, additional programs that 1) vary the movement of background stripes either in the same direction or a different direction from the test pattern's stripes, and 2) increase the number of discrete sequential movements in the same or different directions that are presented before a response is elicited from the subject, are included in the present disclosure.

Multifrequency backgrounds are used to provide a repetitive structure that recruits a larger number of channels tuned to different spatial frequencies, providing a wide structured background frame of reference that reduces background noise by repeating over an area that encompasses the spatial period of the test patterns' movement. In addition to using multifrequency backgrounds to increase the background's complexity, differentially activating a wider range of neural channels in the movement system, the contrast of the background is now increased up to 20% to increase the activation of linked parvocellular neurons after the magnocellular neurons have been sensitized. As lower levels in the dorsal stream are trained so they function normally, the present disclosure then trains subsequently higher levels in the dorsal stream.

Figure 22:
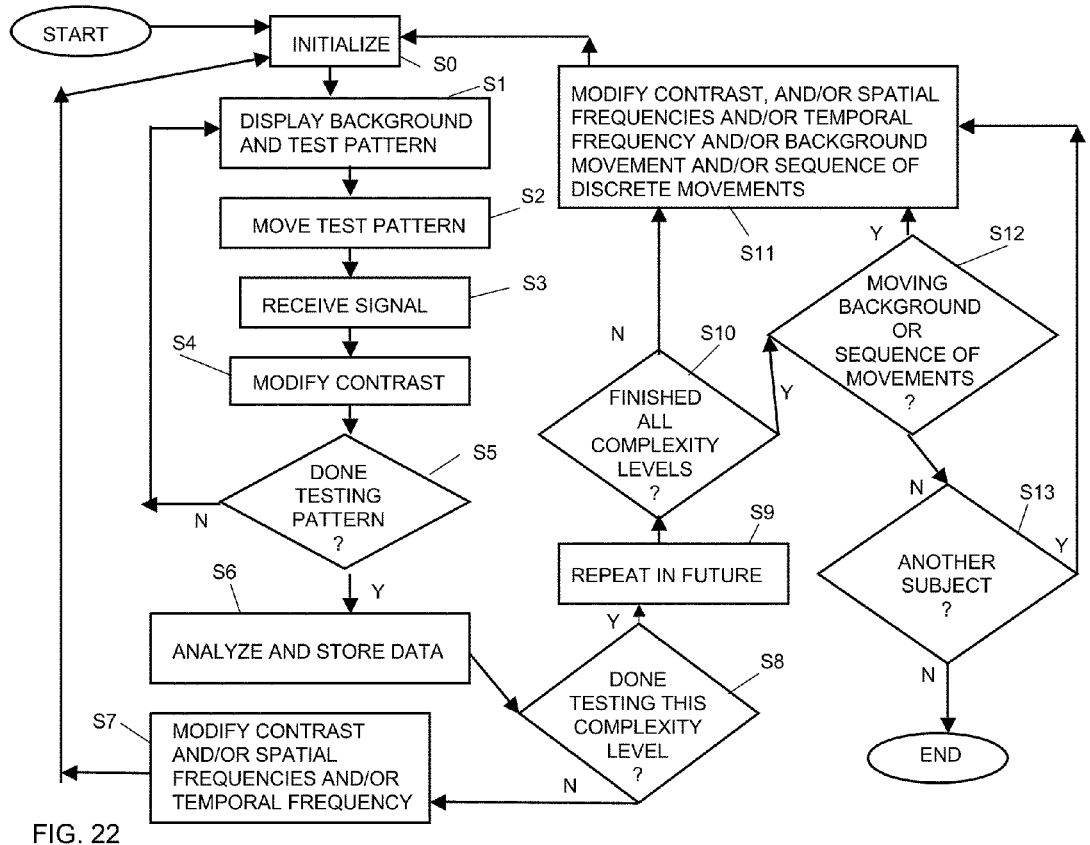
FIG. 22 is a flowchart illustrating steps in exemplary methodology for measuring and improving contrast sensitivity and cognitive skills of a subject in accordance with the present disclosure.

In accordance with the present disclosure, to measure the subject's contrast sensitivity for motion discrimination, the exemplary computer system is configured to implement an interactive process employing a two-alternative forced choice task. The methodology of the present disclosure is generally represented by the flowchart of FIG. 22. All pattern components for the test and background patterns are initialized from a predetermined range of contrasts, spatial and temporal frequencies (blocks S0 and S11). The computer may then generate image files for the test and background pattern in the form of pixel maps or pixmaps. A background and test pattern are displayed (block S1). The test pattern is then moved either in one direction or the opposite direction (block S2). The subject signals which direction the test pattern moved (Block S3). The contrast of the test pattern is adjusted to determine the contrast threshold (Block S4). The preferred embodiment of the present disclosure, again as illustrated in FIG. 22, measures contrast sensitivity for motion discrimination (Blocks S1 to S5) and determines and improves the subject's motion discrimination contrast sensitivity function (CSF) at both low and high levels in the dorsal stream (Block S12). To measure the CSF, a staircase procedure is implemented to measure a contrast-sensitivity threshold for each spatial frequency of the test pattern at each spatial frequency of the background.

Exemplary methodology for measuring contrast sensitivity as illustrated in FIG. 22 may include a plurality of preliminary initial steps, as just described. Generally speaking, the present disclosure measures and improves contrast sensitivity for motion discrimination, which specifically includes direction (i.e. left-right) discrimination. The data for the specified test-pattern spatial frequency may then be stored to generate a contrast sensitivity function (CSF) for the specified test-pattern spatial frequency (Block S6). The contrast, and/or spatial frequencies and/or temporal frequency of the test and background patterns are modified (Block S7). This process is repeated until the subject has been tested for all of the predetermined background-test pattern spatial frequencies at each complexity level (block S8).

If the subject has not been tested for all of the predetermined test-pattern spatial frequencies, after completing the testing for a particular test-pattern, the spatial frequency is modified (Block S7), e.g. increased or decreased with the preferred predetermined range of 0.25 cyc/deg, 0.5 cyc/deg, 1 cyc/deg, and 2 cyc/deg, and the process returns to block S0 in FIG. 22. In addition to the stimulus parameters described in the previous patent, the background contrast, the multiplicity of background frequencies, and the temporal frequency of test and background patterns can be modified by the computer in response to a correct signal, in blocks S7 and S11, at the end of a staircase run for the particular pattern being used. Moreover, the data are analyzed after each replication, block S6, which in the exemplary embodiment consists of 20 patterns to determine if the subject is finished testing at this complexity level, S8. They repeat this process in the future, S9, until they have finished all complexity levels, S10. The computer increases the level of complexity by modifying the background contrast, and/or test and background spatial frequencies, and/or test pattern's temporal frequency, S11.

Figure 4:
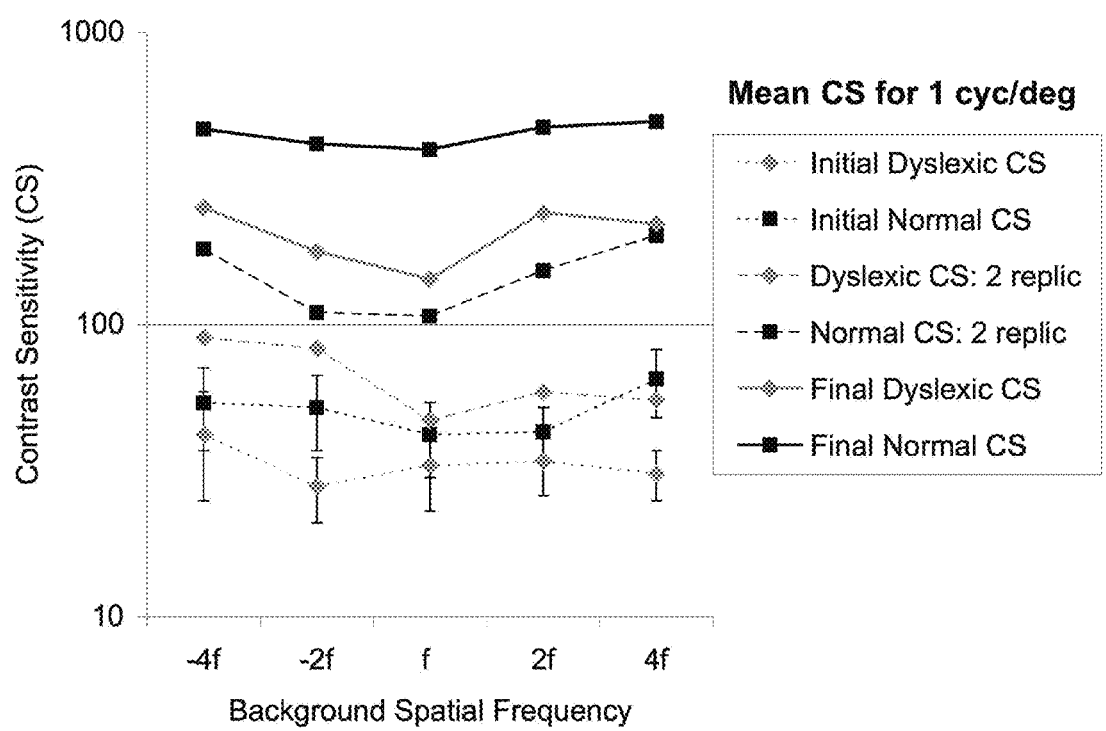
FIG. 4 is a graphical view of data for various subjects, including dyslexic and normal children, illustrating relationships between contrast sensitivity for direction discrimination with respect to spatial frequencies of the background, particularly illustrating that relationship at a spatial frequency of 1 cycle per degree of the test pattern, at the first level of complexity in accordance with the present disclosure.
Figure 5:
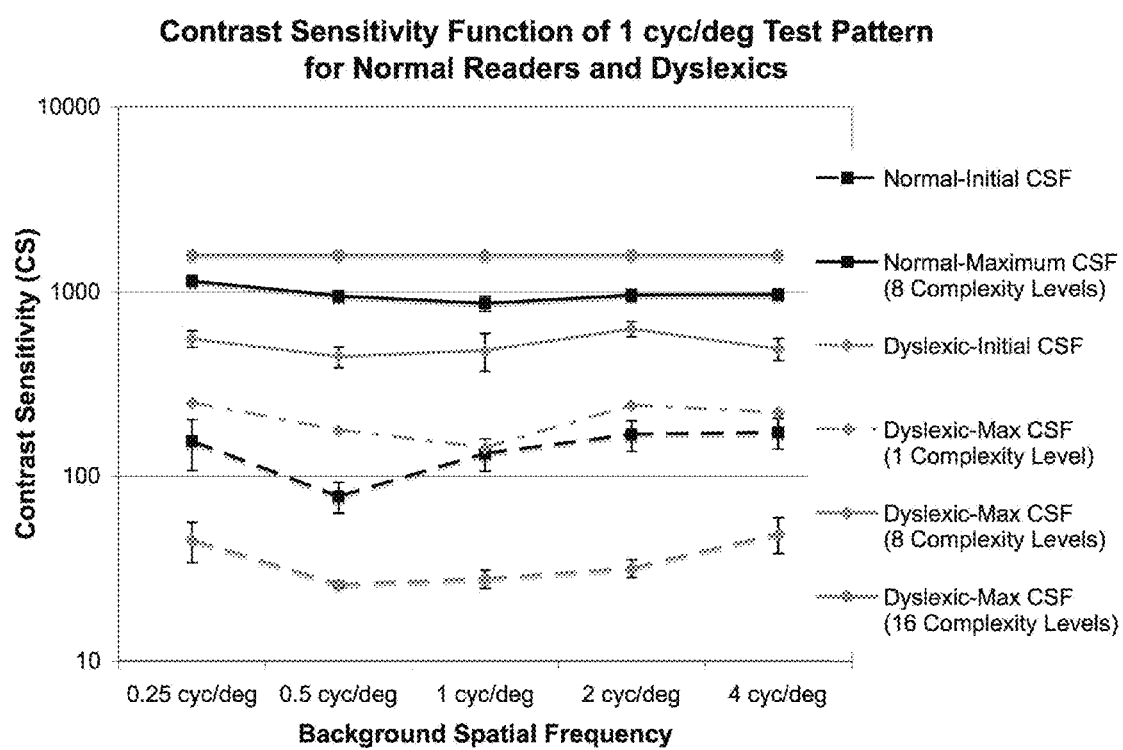
FIG. 5 is a graphical view of data illustrating relationships between contrast sensitivity for direction discrimination with respect to spatial frequencies of the background for various subjects, including dyslexic and normal children, particularly illustrating the relationship at a spatial frequency of 1 cycle per degree of the test pattern, at the first, eighth, and 16th level of complexity in accordance with the present disclosure.
Figure 6:
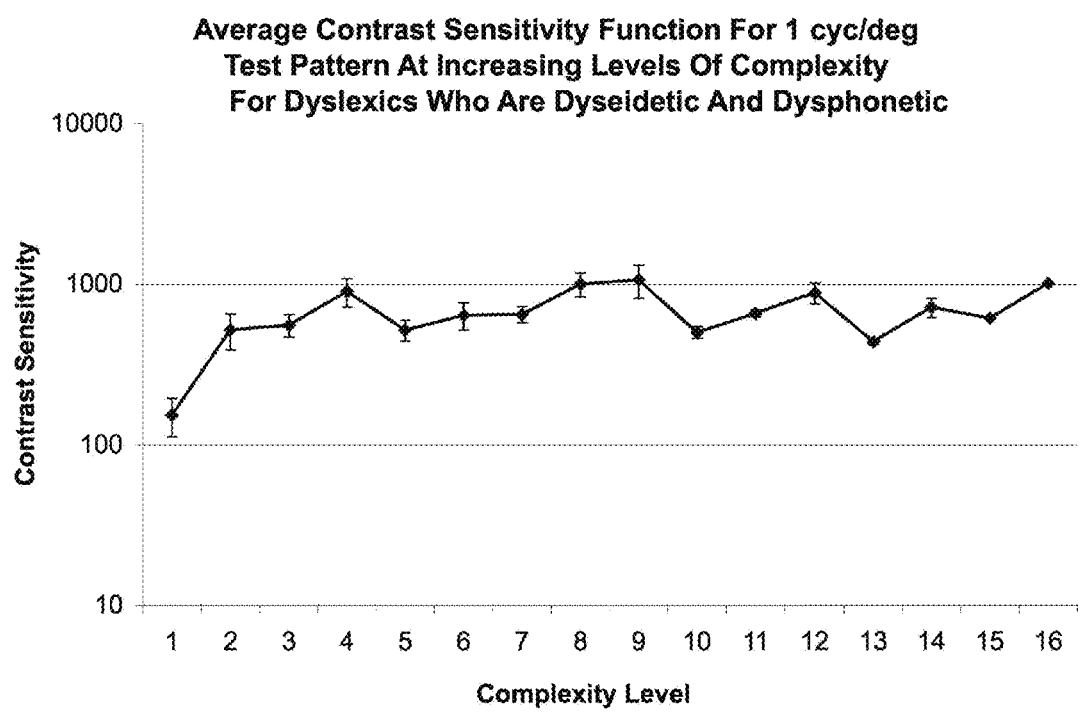
FIG. 6 is a graphical view of data illustrating relationships between contrast sensitivity for direction discrimination when averaged across different spatial frequencies of the background and various subjects, who were dyslexic children, at each level of complexity in accordance with the present disclosure, particularly illustrating the relationship at a spatial frequency of 1 cycle per degree of the test pattern.

The preferred methodology described thus far measures the subject's CSF. In addition, however, the subject's CSF is improved by repeatedly watching the test pattern shift left and right at the predetermined contrast and spatial frequencies. A dyslexic child, for example, would have a CSF like that shown in FIGS. 4 and 5. The process of being tested and identifying the direction of movement during direction discrimination training improves the child's contrast sensitivity. The inventor has discovered that repeating the direction discrimination training (block S4), once or twice a week for 8-12 weeks, significantly improves the CSFs of all children, but especially dyslexic children, so the CSF of a dyslexic child is reshaped to look like that of a normal child (see FIG. 5). The present disclosure, which uses 16 levels of complexity, improves a dyslexic child's contrast sensitivity (FIG. 5) much more than when using just one level of complexity (FIG. 4) with the same number of replications or training sessions (20 patterns). It also improves the CSFs of older adults, improving processing speed, sequential processing, and visual memory (FIGS. 20a-d, 21).

Once the first 16 levels of complexity are completed, Block S10 in FIG. 22, (exemplary levels of complexity are described in FIG. 23), then programs that test higher levels of processing in the dorsal stream may be used (block S12 in FIG. 22). When moving backgrounds are displayed, the same methods and apparatus as described will be used to measure the contrast sensitivity of the test pattern for motion discrimination at higher levels in the dorsal stream. The contrast of the background pattern may equal the contrast of the test pattern. When a sequence of discrete movements are displayed, the contrast is increased if both pattern presentations are not identified correctly. In the preferred embodiment, once a subject is in the two-alternative staircase, the contrast of the test pattern is decreased only when the directions of motion of all patterns in the sequence of discrete movements are identified correctly three times in a row. In the exemplary embodiment, separate keys will be used for each of the pattern alternatives. For example, when two patterns are presented consecutively, then the left arrow key is pushed when the patterns moved left and then right, the right arrow key is pushed when the patterns moved right and then left, the up arrow key when both patterns moved right, and the down arrow key, when both patterns moved left. Once the testing process is completed for one subject, it may be repeated for a plurality of subjects (block S13).

The above-described apparatus and methodology of the present disclosure is capable of being alternatively configured for many applications. For example, rather than being displayed at one to three spatial frequency components, the background may be displayed with a plurality of spatial frequencies, such as in a natural scene. This is particularly beneficial in testing children using the present disclosure, which may be implemented more realistically with the fish-shaped test window "swimming' through a natural aquatic background. Additionally, although the present disclosure has been described in relation to the contrast sensitivity for direction discrimination, the principles of the present disclosure may be readily applied to measuring and improving contrast sensitivity for motion discrimination of the visual cortical movement system using other types of movement, such as expanding and contracting movement, for example, and to improve the timing between the dorsal and ventral streams at different levels of cortical processing to improve speed of processing and widen the attention gateway.

The principles of the present disclosure are further exemplified in the examples that follow.

EXAMPLES

Direction discrimination training uses displays (see FIG. 1) comprising a stationary, central, "fish-like" window surrounded by a stationary, vertically oriented sinewave grating with one or more spatial frequency components. The fish-like window contains a vertical sinewave test grating having a single spatial frequency component. A given trial comprises three frames, each lasting 150 ms for the first 4 levels of complexity listed in FIG. 23. The phase of the test grating on frame 1 is ±45 degrees chosen randomly. On each of frames 2 and 3, the test grating shifts 90 degrees (deg) (¼ of a cycle) in a fixed direction (either rightward or leftward), and the subject's task is to indicate the direction of movement using the right or left arrow keys. A brief, soothing tone is presented after incorrect responses.

The protocol for training left-right movement discrimination comprises the following regimen, using patterns that are optimal for tuning the motion pathway.

(1) Left-right direction discrimination of a sinusoidal test pattern moving relative to a sinusoidal OR a multifrequency background pattern, since multifrequency backgrounds have been shown to increase the range of discriminable patterns at very low contrasts.

(2) 5% background contrast for single and multifrequency gratings, with 10%, and 20% background contrasts for multifrequency gratings, the background contrast changing after each three replications.

(3) Test pattern spatial frequencies of 0.25, 0.5, 1, and 2 cycles per degree.

(4) A test pattern speed of 6.7-13.3 Hz. The pattern moves ¼ cycle, or 90 degrees, every 150 msec-75 msec, (this creates the perception of leftward or rightward movement).

(5) Sinusoidal background patterns of different spatial frequencies, ranging from two octaves below the test pattern to two octaves about the spatial frequency of the test pattern, each background frequency being an octave apart, since neurons in the direction-selectivity network are tuned to approximately one octave.

At the start of the first session, both the test and background gratings are set to 5% contrast, to ensure the pattern's contrast is in the middle of the magnocellular contrast range. Each time the subject correctly identifies the direction the fish (test pattern) stripes move, the contrast of the test grating is lowered until the subject made an incorrect response. The step size varies from 0.3% down to a step size of 0.1% at 0% contrast. Very low contrasts are obtained by special modifications to the computer's color lookup table, varying only one color gun at a time. Although these manipulations might be expected to lead to hue heterogeneities in the stimuli, they are not visible, and, moreover, it is well documented that judgments of motion direction in very low contrast stimuli depend only on luminance variations. Following the first incorrect response, a double-staircase procedure is used to estimate the direction discrimination contrast thresholds. Three successive correct responses reduce the test grating contrast by one step; each error increases the test grating contrast by one step. The staircase terminates after 6 reversals, and the mean of the last 3 is taken to estimate contrast threshold. If the last 3 reversals, where the threshold value should be leveling off, contain 4 or more increments in contrast, the threshold is considered too variable to be reliable, and the contrast threshold is automatically re-measured. Using the last 3 of 6 contrast reversals was found previously to provide the most reliable results compared to using larger numbers of contrast reversals. This staircase procedure estimates the contrast needed for 79% correct responses. Each session takes about 10 minutes to complete. At the end of each staircase run, the trainee receives a score to increase motivation: The lower the contrast threshold, the higher the score.

In a given staircase run, the center spatial frequency is either 0.25, 0.5, 1, or 2 cyc/deg, and the surround grating spatial frequency is either equal to the test frequency or 1 or 2 octaves higher or lower. These stimuli have been found to be optimal for measuring the sensitivity of directionally selective motion pathways. A full training cycle of the left-right movement discrimination task requires 20 threshold determinations (i.e. one for each of the four test spatial frequencies paired with each of the five background spatial frequencies, progressing from 2 octaves below to 2 octaves above the test spatial frequency). Each session covers half a training cycle, consisting of 10 threshold determinations: one threshold for each of two 'test' frequencies displayed within each of five background frequencies. All thresholds involving test spatial frequencies 0.5 and 1 cyc/deg are measured before all thresholds involving test spatial frequencies 2.0 and 0.25 cyc/deg to test easier patterns before the more difficult ones.

Initially, three consecutive 150 msec time intervals are used to present leftward or rightward movement to ensure that this task is easy for dyslexic readers. Even though apparent motion is used, the motion always appears smooth because of the fast speeds. Since initially the sinewave grating moves 90 deg, which is a quarter of a cycle of the spatial period of the center test pattern (one-half a stripe width), in 150 msec, the speed of the test pattern has a constant temporal frequency of 6.7 cycles per second (Hz). In other words, one dark and one light stripe in the fish-like window travel almost two times across the fish body in one second. A constant temporal frequency causes the speed to appear faster for low spatial frequencies, which subtend a wider spatial extent, e.g. test frequencies of 0.25 cyc/deg, than for higher spatial frequencies, which subtend a narrower spatial extent. After each 4 levels of complexity are completed, i.e. on the fifth, ninth, and thirteenth levels, see FIG. 23, the speed of each pattern interval increases by 25 msec, increasing the pattern's temporal frequency up to 13.3 Hz. During this complexity level, the background is a sinewave grating at 5% contrast, with a single spatial frequency component, not increasing to a multifrequency background until the next level of complexity. This is done to train each spatial frequency channel separately first, using contrasts optimal for magnocellular processing, before activating additional spatial frequency channels. Multifrequency backgrounds activate additional spatial frequency channels, increasing the activity of cortical processing. Increasing the contrast of these backgrounds increases the activity of parvocellular neurons, aiding in the integration of magnocellular and linked parvocellular activity.

In addition to the sinewave backgrounds, multifrequency backgrounds (see FIG. 3) consisting of three spatial frequency components bootstrapped to the original sinewave background are used as described above. These frequency combinations facilitate direction discrimination in normal subjects by providing a wide structured background frame of reference that reduces the background noise. Initially, both the test and background frequencies are set to 5% contrast to ensure they were presented well above contrast threshold, yet low enough in contrast so that direction-selectivity is optimized. The level of complexity does not increase until the contrast threshold of the 2 cyc/deg test pattern, the test pattern to which subjects are most sensitive, is less than 1% contrast when averaged across the five background patterns. The computer automatically adjusts the level of complexity.

The following examples investigate whether entertaining visual exercise improves the reading performance of both normal and dyslexic children from ages 5 to 18 years, and the cognitive performance of older adults. The exercise was entertaining because it used a familiar object (i.e. a striped fish) in an unfamiliar way. The subjects' task was to signal whether dim stripes within the fixed fish-shaped window moved to the left or to the right. Visual exercise was provided by using auditory feedback to signal correct and incorrect responses, which enabled the subject to learn to discriminate the directions quickly. These studies revealed the importance of using multiple levels of complexity to keep subjects engaged in the task so their motion discrimination contrast sensitivity, resulting from improving their neural brain timing and thereby their speed of processing, is improved as quickly as possible. These studies also revealed that training motion sensitivity at higher levels in the dorsal stream by using 1) moving backgrounds, and 2) a sequence of discrete movements improved reading speeds even more, as well as improving visual memory, functional field of view, figure/ground discrimination, and sequential processing.

The circuits that underlie motion discrimination are plastic and adapt in response to experience. Accordingly, practicing the task used to measure motion discrimination contrast sensitivity increases the subject's motion contrast sensitivities. To remediate reading disorders, a subject repeats the above-described task for 5 to 10 minutes once or twice a week for about 12 weeks. By using feedback and practice, the subject significantly improves motion discrimination CSFs 44 fold and reading rates 11 fold on average.

Example 1

Studies with Children

Dyslexia can be defined as inefficient word recognition and orthographic skills when spelling phonetically irregular words, and/or as poor phonological skills (how parts of a word sound) when decoding and encoding unfamiliar words. Boder introduced the concept of three categories of dyslexia: 1) dyseidetic (trouble with sight-word recognition and spelling phonetically irregular words such as 'laugh' or 'should'), 2) dysphonetic (trouble sounding out words by word attack), and 3) mixed type (both dysphonetic and dyseidetic). The dyslexia screener, described below, is based on Boder's differentiation of dyslexic children into these three subtypes.

The evidence presented below supports the view that networks in magnocellular streams play a major role in reading and cognitive tasks and are maturing in 5 to 8 year old children. The observation that rapid reading remediation was found using a direction discrimination task, and the most rapid remediation occurred for 6 to 7 year olds, indicates that children are transitioning through a critical period for learning movement discrimination at that age.

Testing was performed on a random sample of second-grade children in four elementary schools in 2002-2003, second- and third-grade children in 2003-2004, and since that time with several individual subjects of ages 5 to 18 years who were diagnosed with dyslexia and referred to the inventor to improve their reading abilities. Children were included in these studies if they had 20/20 visual acuity, normal intelligence, as verified by standardized tests, no known organic disorders, and no known behavioral disorders. Only classrooms where children practiced reading at least 60 minutes each day were included. The children in these studies were a diverse population representative of the range of normal children in each class tested, as verified by each classroom teacher. A total of 107 second-grade children participated in the first study, 106 second- and third-grade children in the second study, and 6 dyslexics who were studied individually. In the controlled validation studies, data were collected during the normal school day, during non-directed reading time, which was usually before directed reading. By testing children during school hours, the study was able to test both normal readers and children with reading problems at regular weekly intervals. In the school studies, each child was tested each morning and in the early afternoon on training days; in the individual studies testing was done immediately after school and before homework was started. Each child was trained on sessions lasting from 5 to 10 minutes once or twice per week for 12-15 weeks.

All subjects sat at a viewing distance of 57 cm (an arm's length) from the screen for all tasks. The contrast and brightness of each computer screen was calibrated using a Pritchard 1980A photometer. To train contrast sensitivity for motion discrimination, only the first level of complexity was used in the first study. In the second, up to 8 levels of complexity were used, and in the studies with individual subjects, 11-16 levels of complexity were used. One classroom of second grade students in the first study also participated in the second study, which enabled determining whether the improvements measured in second grade carried over to third grade.

Standardized tests of reading skills were administered to every subject in these studies. These tests were: 1), A computer-based reading speed assessment (see below); 2), the Dyslexia Determination Test (DDT) in the first study and the Decoding-Encoding Screener for Dyslexia (DESD) for subjects in the second study and for individual subjects; 3), the Wide Range Achievement Test (WRAT-3) reading (word identification) subtest; 4), the WRAT-3 spelling subtest; and 5), the Gray Silent Reading Test (GSRT). The standardized tests were chosen after consulting with leading educational therapists and dyslexia experts as being easy to administer and having high validity in characterizing a student's ability for learning different aspects of reading. The DESD or DDT was used to classify each student as either dyslexic, i.e. inefficient reader, or as an efficient (normal) reader using categories that provide a measure of both the type and severity of the dyslexia: above normal, normal, borderline normal, mildly below normal, moderately below normal, and markedly below normal, in terms of either decoding (pronunciation) and/or encoding (spelling). The reading grade level and the number of words spelled correctly either eidetically or phonologically were used to determine the child's category. The Dyslexia Screener (TDS), an alternate form of the DESD, was validated using the Woodcock-Johnson standardized reading tests. The DESD and the Dyslexia Determination Test (DDT), being a longer version of the DESD, are the only tests available that provide a clinically reliable, differential diagnosis for dyslexia. Furthermore, the DESD reading grade level test is based on a strict, timed, sight-word recognition challenge, as opposed to the WRAT-3 which is not. Note that single word sight-recognition is not necessarily equal to the overall reading grade level of individuals, but tends to be so for dyslexics. This is likely because poor word recognition is the major stumbling block in reading fluency.

Direction discrimination training is hypothesized to improve reading fluency. This dimension of reading skill is most directly measured by the computer-based reading speed assessment. In this test, continuous, non-repeating lines of text from the Frog and Toad series by Arnold Lobel (interesting, easy-to-read stories) for second grade students, and Stuart Little by E. B. White for third grade students were presented on the display six words at a time, so that (1) there was no crowding from adjacent words above or below the line being read, and (2) at least two saccades were required to read each line of text. The text was rendered using large (0.5 cm wide by 0.5 to 0.75 cm high) white sans-serif letters. The six words of white text were centered in a black window, 1.5 cm high by 14.5 cm wide.

The black window was centered in a gray display window that was set to the mean luminance of 50 cd/m2. The child could read the six words of text either as they were being presented or when the presentation was finished. Therefore, the reading rate was not limited by the child's rate of speaking. The experimenter chose a rate of text presentation that was continuous and comfortable for the child. Initially, the speed of presentation was increased from 40 words/min until five out of six words were read incorrectly. At the first incorrect response, a two alternative forced-choice (2AFC) double staircase procedure was implemented, decreasing the speed by one step (12%) each time the text was not correctly identified, and increasing the speed one step only when the child correctly read three successive lines of text. During this task the child was corrected after pronouncing a word incorrectly, and was asked to repeat only the words missed in the six words of text. The same phrase was only shown two times in a row, so that difficult phrases were not a stumbling block. The mean reading-speed threshold was computed from two measurements, each being the mean of the last three out of six reversals in reading speed. This task took about 10 minutes to complete. The relative improvement in reading speed was determined by dividing the final reading speed by the initial reading speed.

The inventor trained and worked with computer laboratory teachers, individual classroom teachers, and teaching assistants who were responsible for administering direction discrimination training in either the computer lab or in the classroom. The inventor also supervised administering the standardized tests at the beginning and end of these studies, with the assistance of teachers and teacher aids in 16 classrooms over the four schools. Group testing in each classroom was used to administer the GSRT and the Spelling subtest of the WRAT-3. Individual testing was used to administer the WRAT-3 word identification task, and either the Dyslexia Screener (DDT) or the DESD. Children were never told the correctness of their responses, but were given positive feedback to encourage them to be relaxed and perform at their abilities. Research assistants measured all computer-based reading rates in the first study and 80% of computer-based reading rates in the second study.

As mentioned above, only children in mainstream classrooms who had normal or above normal intelligence were included in these studies. If a teacher decided to participate, the entire class was included. During the first study assigning children to control groups, which received no intervention other than the schools' regular reading program, was done either randomly or in a counterbalanced fashion. During the second study, control subjects were chosen in this fashion for students in third grade, whereas in two classrooms of second grade students, the students served as their own controls, doing the control therapy after the first 12 weeks and before the second 12 weeks of direction discrimination training (see FIG. 9). During the first study, all children completed 15 replications of the training regimen. During the second study, the 16 classrooms were trained on direction discrimination at different frequencies, enabling a systematic investigation of the effect of increasing the frequency of training on the amounts of improvement found for different reading skills. Also during the second study, some classrooms were trained on direction discrimination only once a week, while during the first study, students were trained on direction discrimination twice a week. As already mentioned, standardized literacy tests were administered at the end of the studies to measure improvements in reading skills.

The validation studies compared 1), training on left-right movement discrimination with 2), training on a 10-minute word discrimination game, and 3), the school's regular reading program. The word discrimination game is a therapy with high potential for improving reading skills. There was no biasing towards one computer game versus the other.

During the second study, the background complexity was increased by using multi-frequency striped gratings, in addition to single-frequency sinewave gratings, to increase the student's motivation to continue playing, and to activate a wider range of visual channels tuned to different spatial frequencies. Children found that since the multifrequency background repeated over a wider area, it anchored the motion discrimination task so it was easier to identify the direction of movement correctly. Direction discrimination training was not administered the same number of times per week in each classroom. Some teachers occasionally administered direction discrimination training twice a week while most administered it once a week. The therapies (computer games) were administered, or played, either in the classroom or in the computer lab, using both iMac computers and PCs.

The intervention therapies were usually administered before directed reading, enabling each child to have plenty of opportunity to practice reading during the school day, and the data were analyzed using either one-factor Analysis of Variance (ANOVA) or t-tests, when only two groups were compared, to determine whether the differences between treatment and control groups were significant.

The raw score on each reading skills test corresponded to a standardized equivalent grade level, where a grade level of 1 comprises 6-year-old students, a grade level of 2 comprises 7-year-old students, and so forth. The equivalent grade level was used to plot the initial and final reading scores and measure the amount of improvement on each of the psychometric tests of literacy. An equivalent grade level was plotted since this is the most relevant information for teachers, school administrators, and parents who take their children to developmental optometrists for vision therapy. The relative improvement in reading skills was determined by comparing the difference between final and initial equivalent grade levels, and/or between the initial and final reading speeds.

During the first study, one-third of the students, comprising both dyslexic and normal readers, were a control group, which played a word discrimination game. During the second, two classes of second graders and one class of third graders, including both dyslexic and normal readers, were the controls. Controls were trained on one of three word discrimination games once a week with each session lasting around ten minutes. Each word game was played on a separate day. The instructions for each word game appeared in writing at the beginning of the game. The first game was the animal game, in which the student pushed the right arrow key if the word was an animal name (e.g. bird) and the left arrow key otherwise. The second game was the name game, in which the student pressed the right arrow key if the word was a person's name and the left arrow key otherwise. All words were in lower case letters. The third game was the nonsense game, in which the student pressed the right arrow if the word was a nonsense word, and the left arrow key otherwise. The child received a score of 5 points for correctly pushing the right arrow key, 2 points for correctly pushing the left arrow key, and lost a point for pushing the wrong key. The word was presented in the middle of the screen until the child pushed either the left or right arrow key. The word then disappeared, a '+' or '−' appeared above the word, and the score was displayed in the upper right corner of the window. The faster the child responded correctly, the faster the words were presented and the higher was their score. This test was timed for 10 minutes and quit automatically when the time was up. The word discrimination game required slightly more attention than did left-right movement discrimination, since the word had to be detected and its category analyzed.

The protocol for training left-right movement discrimination, as described on pages 24-27, was used to provide the intervention therapy in these studies. Two Contrast Sensitivity Functions (CSF) were computed to evaluate the effectiveness of the direction-selectivity training. The initial direction discrimination CSF was determined by the contrast sensitivity after completing the first replication. The final CSF was the maximum contrast sensitivity to discriminate the direction of movement for each test-background pattern combination. The CSF data, stored in individual and summary files, were collected automatically by the computer, which also recorded the level of pattern complexity and the time used to complete each set of five patterns (one-half a session).

Once the subject had completed all 16 levels of complexity using the training regimen described above, the subject then learned to discriminate motion when the backgrounds were moving either in the same direction or in the opposite direction as the test pattern moved. Since both the test and background patterns were moving, the contrast of both were decreased when the subject correctly identified the test pattern's direction of movement. The subject first discriminated movement when the background moved in the same direction as the test, for one session of 10 patterns, and then immediately followed this task by training for one session of 10 patterns on discriminating the direction of movement when the background moved the opposite direction as the test pattern. Sequencing the two tasks in this manner enabled the subject to be trained on the same 10 patterns for each type of background movement, making the tasks easier to complete, as reported by all subjects trained using this protocol. Discriminating the direction of movement with moving backgrounds significantly increased the subject's functional field of view and figure/ground discrimination, subsequently improving all reading skills. When all 8 levels of these two tasks have been completed, then 2 pattern intervals are presented sequentially to improve visual memory. The subject must indicate the direction both patterns moved, i.e. left-left (down arrow), left-right (left arrow), right-right (up arrow) and right-left (right arrow). The contrast threshold is a function of correctly identifying a sequence of discrete movements, contrast only being decreased when the correct arrow key is pushed three times in a row when in the double staircase procedure. This task, which improves visual memory, activates processing in the dorsal lateral prefrontal lobe, the highest level of the cortical hierarchy in the dorsal stream. There are 16 levels of complexity for this task as well.

These changes in the training protocol had dramatically better results than the previous invention using only the first level of complexity. It was found that: 1) the contrast sensitivity for direction discrimination improved significantly more (14-fold instead of 5-fold) with 8 levels of complexity, improving even more (44-fold) with 16 levels of complexity (see FIGS. 2, 3, 4, and 5) the reading rates improved an average of 11-fold with 16 levels of complexity and 4-fold with 8 levels of complexity (FIGS. 8-12) instead of two-fold with one level of complexity (FIG. 7). Only the CSF for test frequencies of 1 cyc/deg were plotted, since this was the most sensitive and representative CSF.

These results suggest that activating a wider range of spatial frequency channels, as ensues from using multifrequency backgrounds and a wider range of background contrasts than used at the first level of complexity provides a more robust and salient frame of reference for direction discrimination. Our working hypothesis in this regard is that a more structured background frame of reference improves the dyslexic reader's ability to discriminate the direction of movement by widening the attention gateway. Increasing the test and background patterns' temporal frequency increases the activation of magnocellular neurons relative to their linked parvocellular neurons. Increasing the patterns complexity in the manner described in FIG. 23, gradually increased the pattern's complexity and the difficulty of completing the task.

Movement direction sensitivity improved with training for both efficient and inefficient readers. The more training children had on direction discrimination, the more their direction discrimination CSF increased, see FIGS. 4, 5. This increase was significant for both dyslexics, p<0.001, and for normal readers, p<0.01. This improvement in their direction discrimination CSF was highly significant even when training consisted of 10 motion games. This improvement was nine to 44 fold for dyslexic subjects and five to seven fold for efficient readers. Therefore, increasing the complexity of the background was an effective training stimulus for improving a subject's motion sensitivity (FIG. 11) at each level of complexity.

These results demonstrate that inefficient readers have immature directionally-selective pathways that develop rapidly following 10 minutes of training on direction discrimination.

Not only was the sensitivity to direction discrimination significantly improved, but the time to discriminate the direction of movement was reduced significantly for both inefficient and efficient readers, p<0.001. The average duration to complete the task (10 pattern contrast thresholds) for both inefficient and efficient readers was reduced from an initial duration of 15 minutes down to 7-8 minutes by the second replication for all students in these studies. Therefore, direction discrimination training improves each subject's speed of processing.

Figure 8:
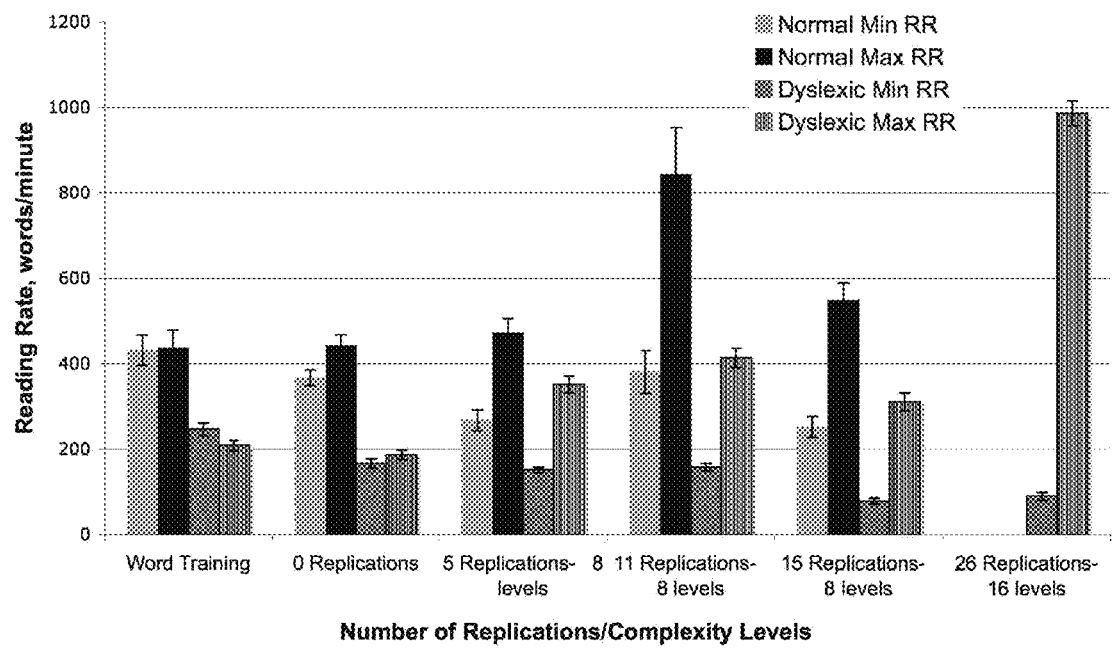
FIG. 8 is a graphical view of data illustrating relationships between reading rates with respect to different training regimens, number of replications, and levels of complexity for dyslexic and normal subjects.
Figure 9:
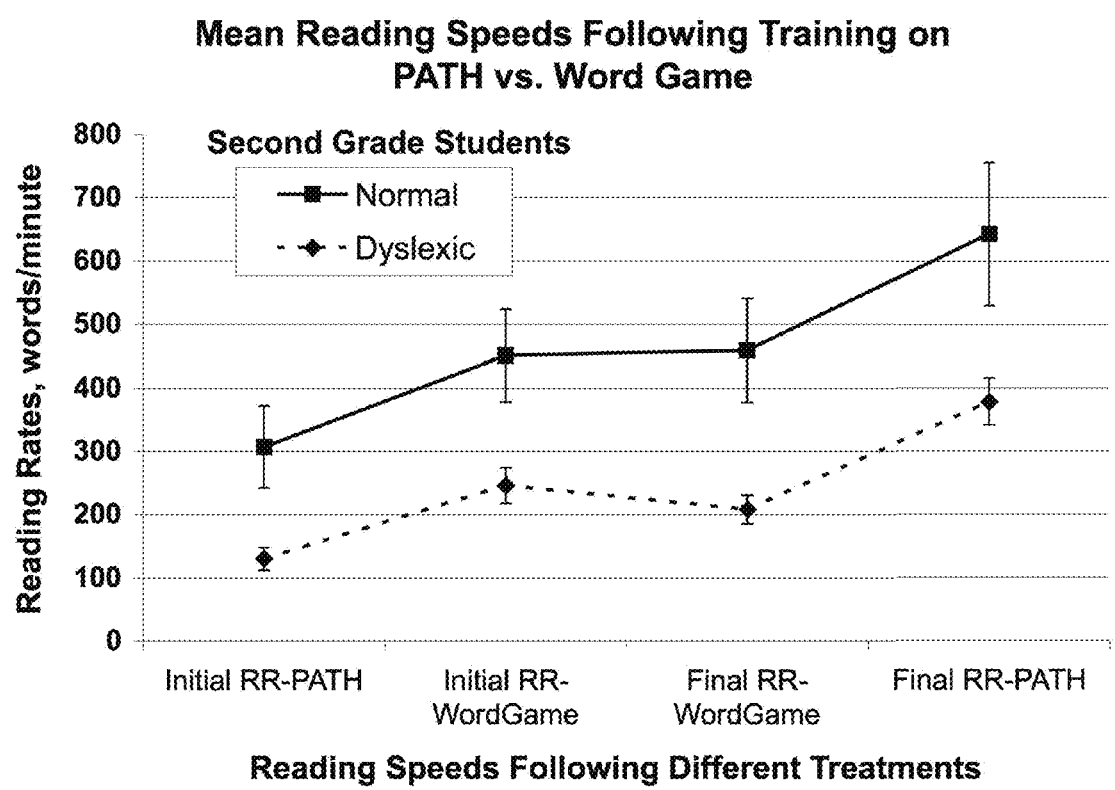
FIG. 9 is a graphical view of data illustrating relationships for reading speeds for second grade students initially, before direction discrimination training, after 12 weeks of direction discrimination training that was right before being trained on the word game, immediately following the word game training, and after the second 12 weeks of direction discrimination training at the end of the study.
Figure 10:
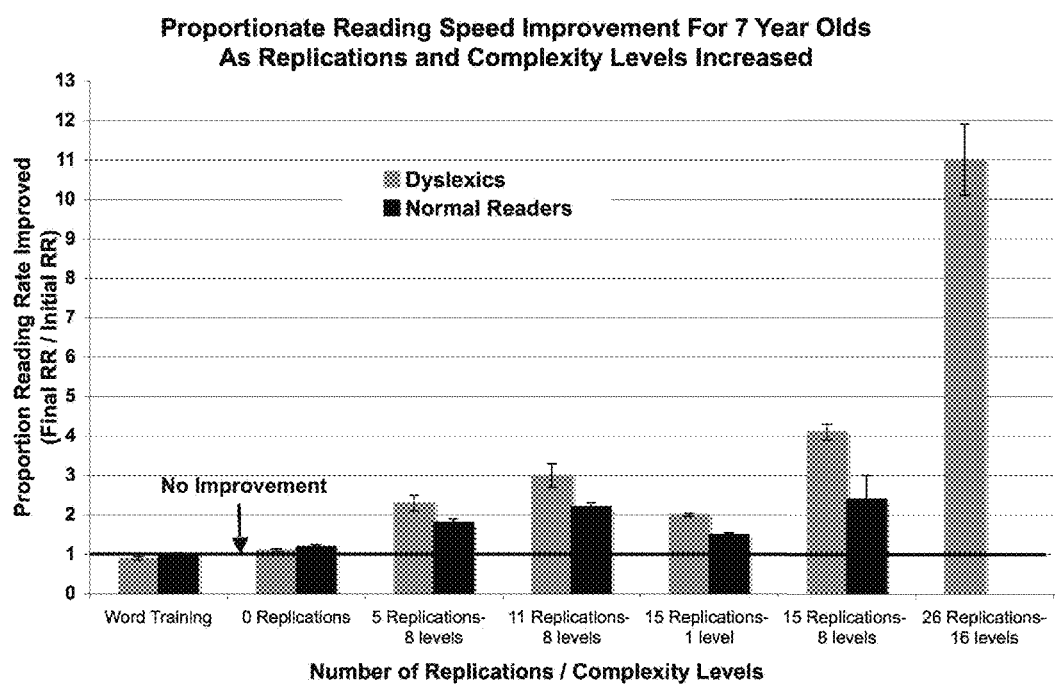
FIG. 10 is a graphical view of data illustrating relationships between proportionate improvement in reading rates with respect to different training regimens, number of replications, and levels of complexity for dyslexic and normal subjects, aged seven years on average.
Figure 11:
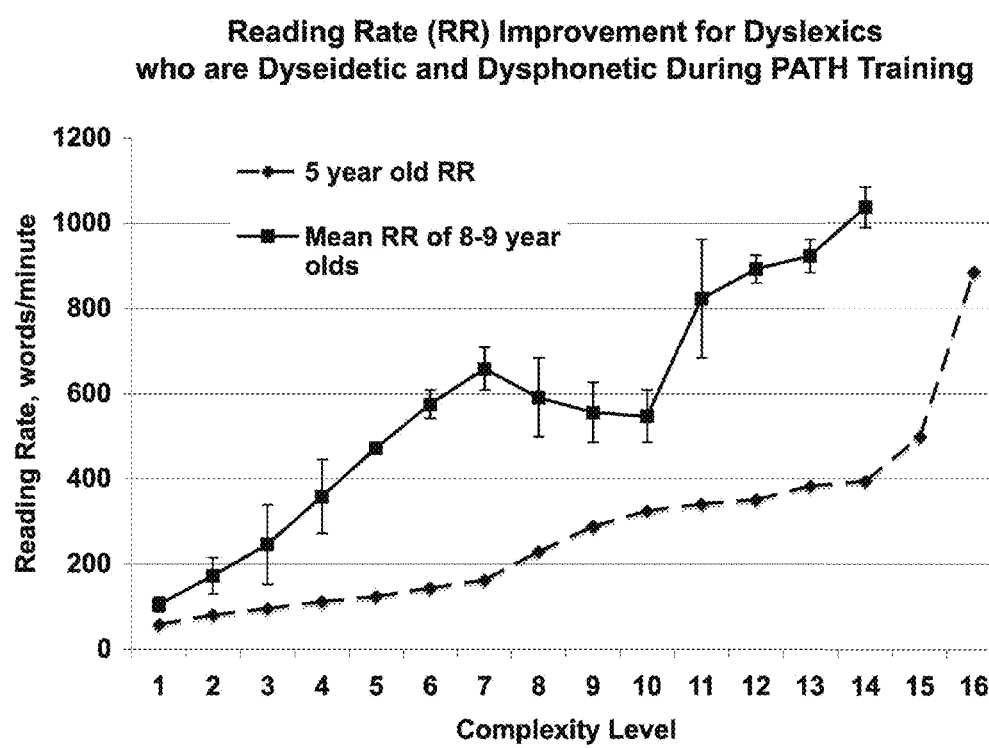
FIG. 11 is a graphical view of data illustrating relationships between reading rates with respect to different levels of complexity for dyslexic subjects who are also dyseidetic, and dysphonetic.

The central hypothesis driving the current study was that direction discrimination training is more effective at increasing reading fluency than either no training (aside from the reading program offered by the school) or training in the word game. Dyslexic subjects trained using left-right movement improved substantially more in reading fluency than did dyslexic subjects in the two control groups (FIGS. 7-10). When the word game was played, then reading fluency did not improve for either inefficient or efficient readers (FIGS. 8-10). These results were highly significant for both inefficient and efficient readers, p<0.001. The more often inefficient and efficient readers were trained on direction discrimination (FIGS. 8-12), the more they improved in reading fluency. There were significant improvements in reading fluency with 8 levels of complexity, a doubling (two-fold increase) after 5 replications, a three-fold increase after 11 replications, and a 4-fold increase after 15 replications, whereas after 15 replications with 16 levels of complexity and 26 replications, reading fluency improved 11-fold which was significantly more. Efficient readers also improved significantly in reading fluency, doubling in reading fluency after 15 replications with 8 levels of complexity. Inefficient readers improved in reading speed significantly more than did efficient readers in both second and third grade, p<0.001, in part, because inefficient readers began at a much slower reading speed than found for efficient readers. The remediation is maintained over time (FIG. 12).

Not only did reading fluency improve when students trained themselves to discriminate the direction of motion at low contrasts, but word identification (FIG. 13, 14), reading comprehension (FIG. 15) and spelling (FIG. 16) also improved for inefficient readers in second grade, p<0.001, and third grade, p<0.01. Training direction discrimination improved not only a child's contrast sensitivity for movement discrimination and speed of processing, but also reading fluency and a wide range of reading skills.

In addition to direction discrimination training helping children who were dyslexic, it significantly improved reading fluency in children who were amblyopic, enabling the two eyes to work together more easily (FIGS. 17-19), autistic, or who had Traumatic Brain Injury (see FIG. 19). These results demonstrate that direction discrimination training improves reading fluency in a wide range of vision and cognitive disorders.

Example 2

Studies with Older Adults

Direction discrimination training can be used not only to improve reading skills in children, but can also improve cognitive skills in older adults. As people age, some brain functions are diminished, especially the speed of information processing. These processing speed deficits are thought to underlie the cognitive decline that older adults experience. Moreover, the prevalence of speed of processing deficits increases with age. Direction discrimination training, combined with object recognition significantly improved processing speed and performance in driving and other mobility and navigation tasks.

This study determined whether training on direction discrimination would improve the ability of older adults to discriminate the direction of motion and speed of processing, thereby improving visual and higher cognitive functions, i.e.—driving and navigation. The older adults in this study reported that in the past they had experienced a decreased functional field of view, tunnel vision, when driving. Furthermore, they also reported a decrease in their field of view when engaged in working memory tasks, e.g. in their employment.

As they aged, a narrowed field of view was the primary way to focus their attention, thereby reducing the effort needed to complete a task by limiting the amount of information to be processed. With training, these older adults found their usable field of view improved, thus enabling them to see much more in a single glance and with much more clarity. They also experienced better figure/ground discrimination, and improvements in navigation, e.g. driving in general, but more so when driving at dusk and at night. Working memory was reportedly improved by all subjects, thus reducing confusion on the job and the ensuing stress associated with information overload.

A vision questionnaire was administered, one adapted from the Low-Luminance Questionnaire, to determine who was at risk for having problems with motion discrimination. As a result of their responses, seven older adults, aged 55 to 74, were recruited to participate in this study. Their motion discrimination deficits were verified by careful psychophysical measurements, i.e. the first session of direction discrimination training. All subjects had visual acuity correctable to 20/20, and had age appropriate ocular media changes.

The same protocol for training left-right movement discrimination that is described on pages 19-20 was used in this study as well. There were 16 levels of complexity, as defined in FIG. 23. The level of complexity did not increase until the mean contrast threshold of the 2 cyc/deg test pattern, the pattern to which subjects were most sensitive to direction of movement, also seen in FIGS. 20d and 21 was less than 1% contrast. The level of complexity was adjusted automatically by the computer. All direction discrimination training was administered by a vision therapist.

Contrast Sensitivity Functions (CSF) were computed to evaluate the effectiveness of the direction-selectivity training. The initial direction discrimination CSF was determined by the contrast sensitivity after completing the first replication. The subsequent CSFs were the maximum contrast sensitivity to discriminate the direction of movement for each test-background pattern combination at each level of complexity, from 1 to 16. The patients averaged twelve weeks of training, each having two sessions twice a week. One patient trained for 16 weeks and two for 11 weeks. The other 4 patients completed direction discrimination training in 12 weeks. Following the completion of training, each subject was interviewed to assess their improvements in reading, figure/ground discrimination, sequential memory, field of usable vision, and ability to navigate. Each subject was asked to report any changes they had noticed since direction discrimination training began.

Figure 20A:
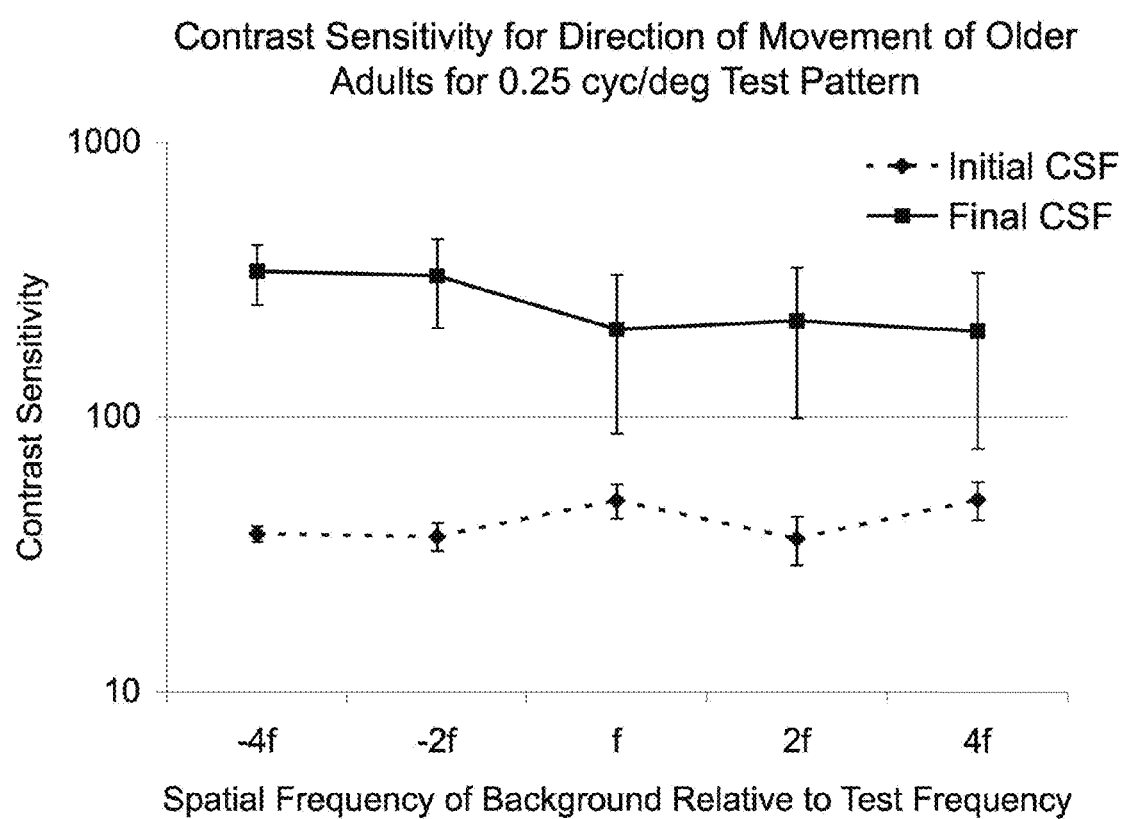
FIGS. 20a-d are graphical views of data illustrating relationships between contrast sensitivity for direction discrimination with respect to spatial frequencies of the background for various subjects, who are older adults, particularly illustrating the relationship of the test pattern at a spatial frequency of 0.25 cycle per degree, 0.5 cycle per degree, 1 cycle per degree, and 2 cycles per degree, in that order.
Figure 20B:
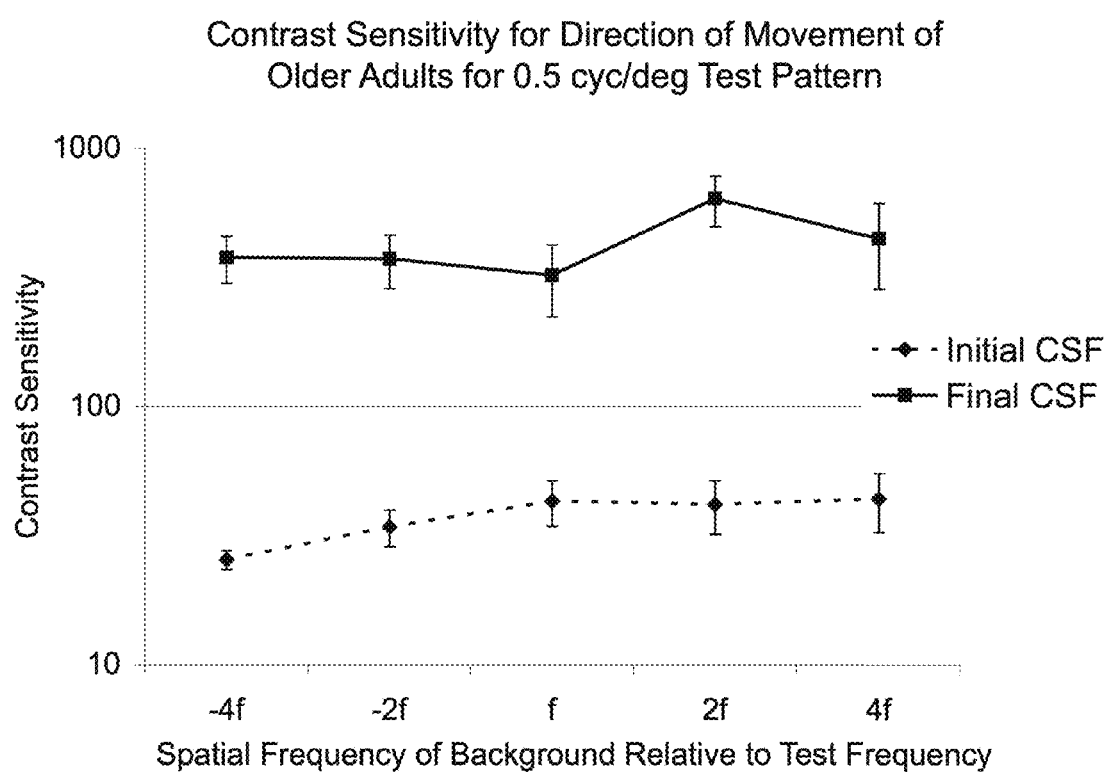
Figure 20C:
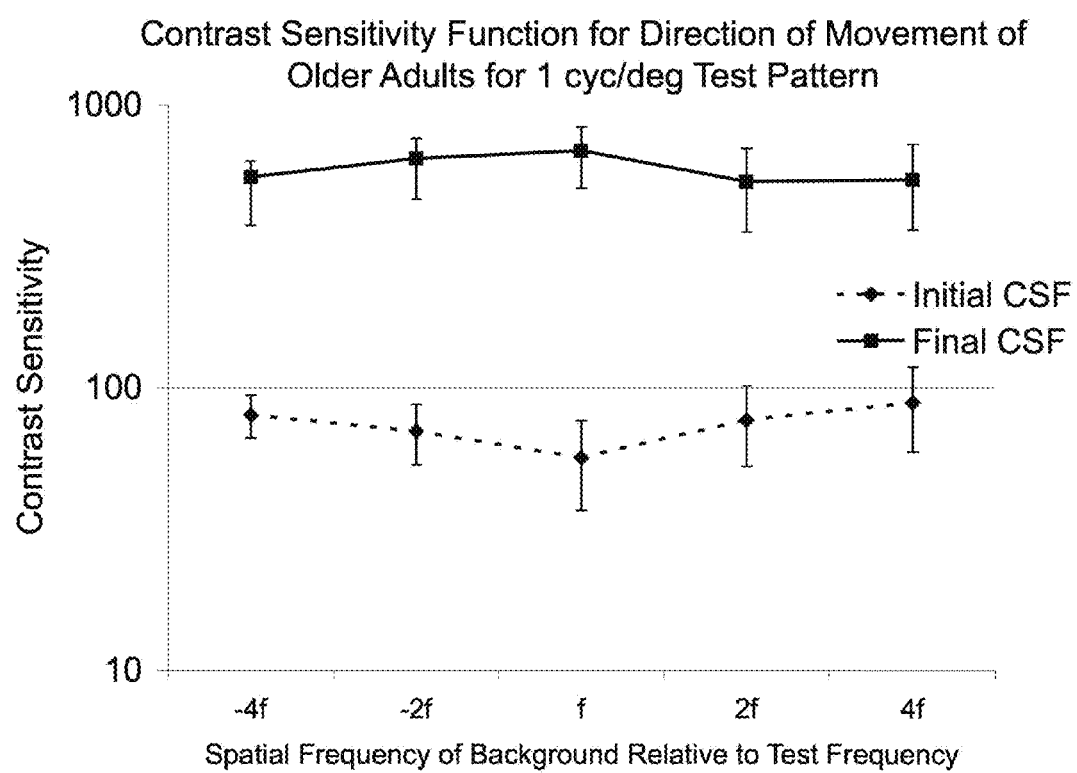
Figure 20D:
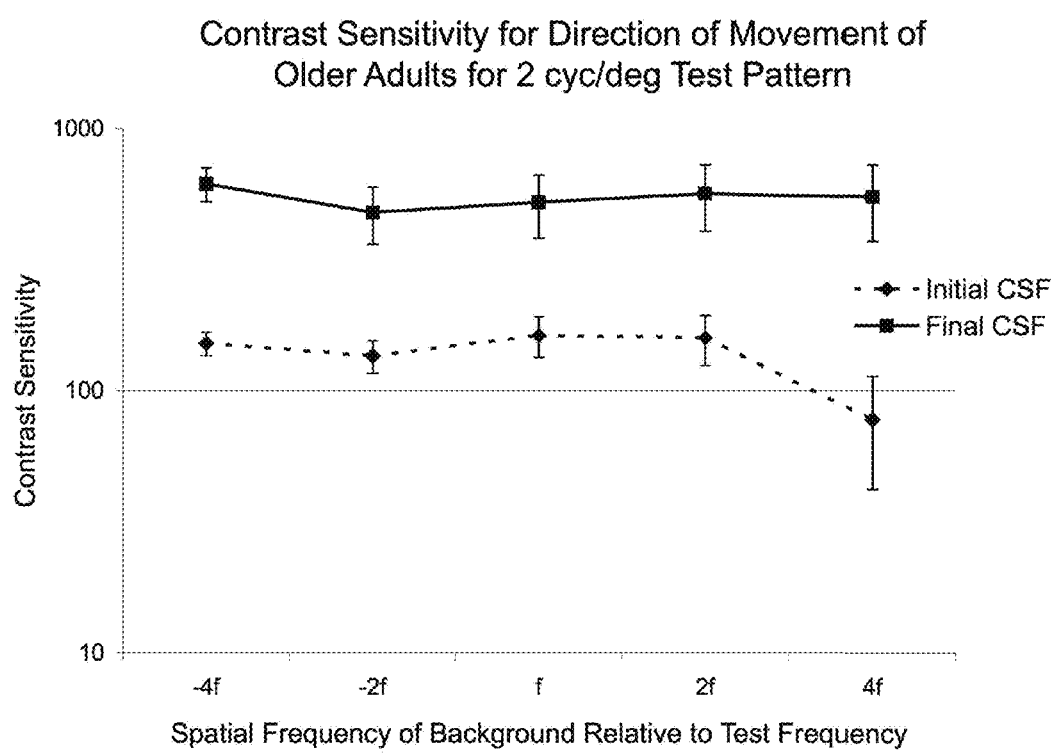
Figure 21:
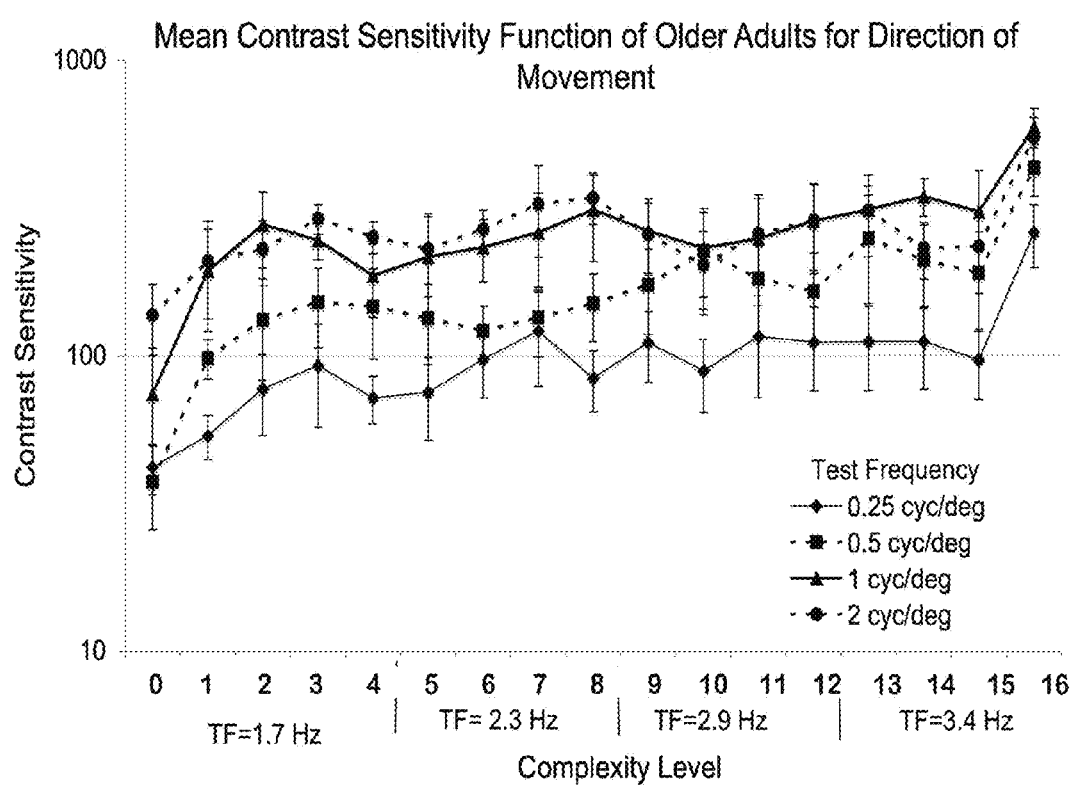
FIG. 21 is a graphical view of data illustrating relationships between contrast sensitivity for direction discrimination on each replication with respect to spatial frequencies of the test pattern for various subjects, who are older adults, when data were averaged across each of the 5 background frequencies.

The low initial Contrast Sensitivity Functions (CSFs) improved significantly following direction discrimination training, see FIGS. 20a-d, an average of 7 fold. Except for the large jumps in CSF at the beginning and end of the training, the improvements in CSF were gradual as shown in FIG. 21. When analyzed using a two-factor ANOVA, $F(16,3)=18.02$, 83.8, $p<0.00001$, each person's CSF improved significantly over the course of training for each of the four test frequencies. This high level of significance shows that 7 subjects were sufficient to generate the statistical power needed for this analysis. In FIG. 21, the initial CSF before training is labeled complexity level 0. Each higher level of complexity corresponds to the level listed in FIG. 23. Since the CSF is most directly related to the output response of directionally selective motion neurons, improvements in a subject's CSF reflect an improvement in the sensitivity of these motion-tuned cells. Test patterns of 1 and 2 cyc/deg had the highest CSFs, as found for children.

It is striking that the largest jump in sensitivity occurs initially and at the highest level of complexity (FIG. 21). It is likely this occurs initially, because the timing in the dorsal stream is changing. Furthermore, it is likely this occurs at the highest level, since this stimulus combination maximizes interactions between magnocellular and parvocellular pathways, having the fastest temporal frequency, 13.3 Hz, and highest background contrast, 20%. After each direction discrimination training session, subjects reported concomitant improvements in the usable field of view and the saliency of improved figure-ground discrimination, as well as their ability to remember and navigate. Moreover, the CSF for each of the test frequencies shows that the direction of movement of 1 and 2 cyc/deg patterns are seen most easily, having a higher CSF across complexity levels (FIG. 21). Subjects required more contrast to discriminate the direction of movement between test patterns below 1 cyc/deg, the lowest spatial frequency tuned channel found in people, with more contrast needed as the test frequency decreased. In fact, the CSF improved the most for the 1 cyc/deg test pattern initially, and over the course of training when test and background frequencies were equal, as shown in FIGS. 20c and 21. It is likely that discriminating the direction of movement for bars wider than 1 cyc/deg required pooling information across channels tuned to a range of spatial frequencies. Subjects all found discriminating the direction of 0.25 cyc/deg test patterns hardest to do initially and easiest after the first month of direction discrimination training. However, the CSFs were always lowest for the 0.25 cyc/deg pattern as seen in FIGS. 20a and 21, showing that the visual system of older adults is less sensitive to the motion of very low spatial frequency patterns.

After the first month of direction discrimination training, all subjects reported noticing significant improvements in their field of usable vision, figure-ground discrimination, working memory, and navigation, especially at night. These responses were provided when asked to report any changes they had noticed, for example, in their vision, memory, or ability to drive, since starting their direction discrimination training, and were not the result of asking specific questions. In addition, subjects also reported that these tasks now required much less effort. Moreover, for all subjects, none of these improvements have regressed over time.

The uniqueness of the approaches exemplified above to investigate vision, reading, and cognitive skills is based on seven different lines of evidence:

First, these studies found increasing the pattern complexity from single to multifrequency patterns was the next step in complexity needed to increase the difficulty of the task, recruiting additional spatial frequency channels to consolidate the increase in movement sensitivity across single neural channels in visual cortex area V1 and the movement area MT. Using the bootstrapping method, described previously, to determine the frequency composition of these multifrequency gratings is unique by reducing the background noise. The bootstrapping method insures the background has a low fundamental frequency, that repeats over an area encompassing the spatial period of the test patterns' movement by either 1) equaling the fundamental frequency of the sinewave background grating when the spatial frequency of the background is lower than or equal to the spatial frequency of the test frequency, or 2) lowering the fundamental frequency of the background to be equal to that of the test pattern's spatial frequency when the first background frequency component is higher than the test frequency. The background structure created by this bootstrapping method enables a wider range of linked parvocellular activity to be used as a frame of reference for movement discrimination, improving the timing in the dorsal stream more than possible with the original invention.

Second, increasing the contrast of the backgrounds enables progressively more interactions between magnocellular and parvocellular activity providing a means to better synchronize their activities, increasing the difficulty of the task. Therefore, increasing the background contrast provides a second method for entraining a wider range of linked parvocellular neurons with the magnocellular neurons used for direction discrimination.

Third, increasing the temporal frequency of the test and background patterns after increasing the contrast of background multifrequency gratings enables successively increasing magnocellular activity relative to linked parvocellular activity, from 6.7 to 13.3 Hz, being long enough to transmit parvocellular activity to the cortex, yet short enough so that training is centered around the optimal speed of magnocellular neurons. If a pattern's temporal frequency were increased too quickly, before a multitude of different spatial channels were sensitized by increasing the contrast of multifrequency backgrounds, then reading rates decreased, instead of increasing. Therefore, the order in which the complexity of the patterns are increased is fundamental to direction discrimination training, providing efficacious reading remediation. Moreover, systematically decreasing the presentation intervals, as is done in the present disclosure, further improves speed of processing.

Fourth, having the backgrounds move in addition to the test pattern after the subject was trained on the initial 16 levels of complexity increases the effectiveness of direction discrimination training considerably, increasing not only attention, speed of processing, figure/ground discrimination, sequential processing, but also the functional field of view.

Fifth, having a sequence of discrete movements be presented before the subject responds increases the effectiveness of direction discrimination even more, training the dorsal stream at the highest level, i.e. at the anterior portion, located in the frontal lobes, improving all of the above reading and cognitive skills, in addition to visual memory.

Sixth, the present disclosure enables diagnosing and remediating not only those who have reading difficulties, but also those with cognitive decline, due to aging, for example. The present disclosure improves the reading performance of both dyslexic and normal children who are learning to read, providing developmental training by tuning their neural timing and speed of processing. Subsequently, fewer children will be classified as special needs children in third grade. There is no other therapy to improve an adult's contrast sensitivity to motion discrimination at various levels in the dorsal stream, resulting in their having improved speed of processing and a broader attention gateway. Direction discrimination training has a broad benefit to society, improving people's long-term productivity and quality of life and thereby saving a great deal of money, time, and effort.

This unique approach provides strong evidence that the brain's inhibitory and excitatory networks that are mediated by magnocellular neurons in conjunction with linked parvocellular neurons play a major role in reading, both in directing eye movements to pattern onset, but also in word recognition and comprehension. Improvements in these areas lead to striking improvements in spelling, pronunciation, desire to read, learning, and self-esteem and, in adults to improving higher level cognitive skills such as attention, sequential processing, navigation, figure/ground discrimination, functional field of view, and visual memory.

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

One possible variation on what has been described above is to use a Wii game system, instead of the proposed computer system to implement the different computer instructions so that 3-D movement is combined with the visual training of brain pathways to improve movement discrimination at different levels of processing in the brain. Another possible variation on what has been described above is to use a wireless phone, with access to the internet that has streaming video input, to implement the different computer instructions so the visual training of brain pathways to improve movement discrimination at different levels of processing in the brain can be done in any location desired. Another possible variation on what has been described above is to use a high definition TV or a 3-Dimensional TV system with a dedicated circuit to implement the different computer instructions so that 3-D movement is combined with the visual training of brain pathways to improve movement discrimination at different levels of processing in the brain.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases in a claim mean that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

The invention claimed is:

1. Computer-readable storage media containing computer readable code which, when loaded into a computer system having a processing system and a user interface including a display, causes a method to be implemented which helps remediate a cognitive defect of a subject, the method comprising in the order recited:

displaying to the subject on the display:

a background which includes a pattern which has visibly lighter portions and darker portions that visibly vary in luminance across a spatial dimension at multiple spatial frequencies; and a test pattern which has a lighter portion and a darker portion moving in one or more directions within the boundaries of the background;

receiving a communication from the subject through the user interface indicating the direction or directions in which the test pattern appears to the subject to have moved; and repeating the displaying and the receiving steps associated with the background and the test pattern a plurality of times.

2. The computer-readable storage media of claim 1 further comprising changing the contrast of the background during the method.

3. The computer-readable storage media of claim 2 wherein the contrast of the background does not exceed 20% during the method.

4. The computer-readable storage media of claim 1 wherein the test pattern has a single spatial frequency and wherein each of the multiple spatial frequencies of the background are a harmonic of the spatial frequency of the test pattern.

5. The computer-readable storage media of claim 1 wherein the contrast of the test pattern does not exceed 10% during the method.

6. Computer-readable storage media containing computer readable code which, when loaded into a computer system having a processing system and a user interface including a display, causes a method to be implemented which helps remediate a cognitive defect of a subject, the method comprising in the order recited:

displaying to the subject on the display:
a background which includes a pattern which has a lighter portion and a darker portion; and
a test pattern which has a lighter portion and a darker portion moving in one or more directions within the boundaries of the background;

receiving a communication from the subject through the user interface indicating the direction or directions in which the test pattern appears to the subject to have moved;

repeating the displaying and the receiving steps associated with the background and the test pattern a plurality of times while changing the temporal frequency of the test pattern by changing the rate at which the test pattern moves, based on the accuracy of the communications received from the subject about the direction or directions of the test pattern.

7. The computer-readable storage media of claim 6 wherein the temporal frequency of the test pattern does not exceed 30 Hz during the method.

8. The computer-readable storage media of claim 6 wherein the contrast of the test pattern does not exceed 10% during the method.

9. Computer-readable storage media containing computer readable code which, when loaded into a computer system having a processing system and a user interface including a display, causes a method to be implemented which helps remediate a cognitive defect of a subject, the method comprising in the order recited:

displaying to the subject:
a background which includes a pattern which has a lighter portion and a darker portion; and
a test pattern which has a lighter portion and a darker portion moving only in a first direction within the boundaries of the background;

receiving a communication from the subject through the user interface indicating the direction or directions the test pattern appears to the subject to have been moved;

displaying to the subject:
a background which includes a pattern which has a lighter portion and a darker portion; and
a test pattern which has a lighter portion and a darker portion moving only in a second direction within the boundaries of the background, the second direction being opposite of the first direction;

receiving a communication from the subject through the user interface indicating the direction or directions the test pattern appears to the subject to have been moved;

displaying to the subject:
a background which includes a pattern which has a lighter portion and a darker portion; and
a test pattern which has a lighter portion and a darker portion moving only in the first and then the second direction within the boundaries of the background;

receiving a communication from the subject through the user interface indicating the direction or directions the test pattern appears to the subject to have been moved;

displaying to the subject:
a background which includes a pattern which has a lighter portion and a darker portion; and
a test pattern which has a lighter portion and a darker portion moving only in the second and then the first direction within the boundaries of the background; and receiving a communication from the subject through the user interface indicating the direction or directions the test pattern appears to the subject to have been moved.

10. The computer-readable storage media of claim 9 wherein the contrast of the test pattern does not exceed 10% during the method.

11. The computer-readable storage media of claim 9 further comprising changing the contrast of the test pattern during the method based on the accuracy of the communications received from the subject about the direction or directions of the test pattern.

12. The computer-readable storage media of claim 11 further comprising changing the temporal frequency of the test pattern during the method based on the accuracy of the communications received from the subject about the direction or directions of the test pattern.

13. The computer-readable storage media of claim 12 further comprising changing the contrast of the background during the method based on the accuracy of the communications received from the subject about the direction or directions of the test pattern.

14. The computer-readable storage media of claim 9 wherein the background includes a pattern which has visibly lighter portions and darker portions that visibly vary in luminance across a spatial dimension at multiple spatial frequencies.

15. The computer-readable storage media of claim 9 further comprising changing the temporal frequency of the test pattern by changing the rate at which the test pattern moves, during the method based on the accuracy of the communications received from the subject about the direction or directions of the test pattern.

16. The computer-readable storage media of claim 9 further comprising changing the contrast of the background during the method based on the accuracy of the communications received from the subject about the direction or directions of the test pattern.

17. The computer-readable storage media of claim 9 wherein the background includes a pattern which has a lighter portion and a darker portion that visibly vary in luminance across a spatial dimension at multiple spatial frequencies.

* * * * *